US010098845B2

(12) United States Patent
Hsu et al.

(10) Patent No.: US 10,098,845 B2
(45) Date of Patent: *Oct. 16, 2018

(54) MUCO-ADHESIVE, CONTROLLED RELEASE FORMULATIONS OF LEVODOPA AND/OR ESTERS OF LEVODOPA AND USES THEREOF

(71) Applicant: Impax Laboratories, Inc., Hayward, CA (US)

(72) Inventors: Ann Hsu, Hayward, CA (US); Liang C. Dong, Hayward, CA (US); Amy Ding, Hayward, CA (US); Suneel Gupta, Hayward, CA (US)

(73) Assignee: IMPAX LABORATORIES, LLC, Hayward, CA (US)

( * ) Notice: Subject to any disclaimer, the term of this patent is extended or adjusted under 35 U.S.C. 154(b) by 53 days.

This patent is subject to a terminal disclaimer.

(21) Appl. No.: 15/027,654

(22) PCT Filed: Oct. 7, 2014

(86) PCT No.: PCT/US2014/059554
§ 371 (c)(1),
(2) Date: Apr. 6, 2016

(87) PCT Pub. No.: WO2015/054302
PCT Pub. Date: Apr. 16, 2015

(65) Prior Publication Data
US 2016/0250170 A1 Sep. 1, 2016

Related U.S. Application Data

(60) Provisional application No. 61/887,762, filed on Oct. 7, 2013.

(51) Int. Cl.
| | | |
|---|---|---|
| *A61K 9/48* | (2006.01) | |
| *A61K 9/16* | (2006.01) | |
| *A61K 9/50* | (2006.01) | |
| *A61K 31/198* | (2006.01) | |
| *A61K 9/00* | (2006.01) | |
| *A61K 31/216* | (2006.01) | |
| *A61K 45/06* | (2006.01) | |

(52) U.S. Cl.
CPC .......... *A61K 9/4808* (2013.01); *A61K 9/0053* (2013.01); *A61K 9/1652* (2013.01); *A61K 9/5026* (2013.01); *A61K 9/5042* (2013.01); *A61K 9/5073* (2013.01); *A61K 31/198* (2013.01); *A61K 31/216* (2013.01); *A61K 45/06* (2013.01)

(58) Field of Classification Search
None
See application file for complete search history.

(56) References Cited

U.S. PATENT DOCUMENTS

| | | |
|---|---|---|
| 3,891,696 A | 6/1975 | Bodor et al. |
| 4,021,555 A | 5/1977 | Seyfried et al. |
| 4,160,020 A | 7/1979 | Ayer et al. |
| 4,367,217 A | 1/1983 | Gruber et al. |
| 4,424,235 A | 1/1984 | Sheth et al. |
| 4,427,648 A | 1/1984 | Brickl et al. |
| 4,438,091 A | 3/1984 | Gruber et al. |
| 4,826,875 A | 5/1989 | Chiesi |
| 4,832,957 A | 5/1989 | Dempski et al. |
| 4,839,177 A | 6/1989 | Colombo et al. |
| 4,849,227 A | 7/1989 | Cho |
| 4,855,326 A | 8/1989 | Fuisz |
| 4,938,968 A | 7/1990 | Mehta |
| 4,963,590 A | 10/1990 | Backstrom et al. |
| 4,900,755 A | 12/1990 | Dempski et al. |
| 5,051,262 A | 9/1991 | Panoz et al. |
| 5,135,950 A | 8/1992 | Pippuri et al. |
| 5,112,861 A | 12/1992 | Backstrom et al. |
| 5,188,840 A | 2/1993 | Iida et al. |
| 5,449,194 A | 8/1995 | Backstrom et al. |
| 5,487,901 A | 1/1996 | Conte et al. |
| 5,532,274 A | 7/1996 | Wenzel et al. |
| 5,576,022 A | 11/1996 | Yang et al. |
| 5,594,030 A | 1/1997 | Conte et al. |
| 5,624,960 A | 4/1997 | Wenzel |
| 5,637,320 A | 6/1997 | Bourke et al. |
| 5,650,169 A | 7/1997 | Conte et al. |

(Continued)

FOREIGN PATENT DOCUMENTS

| | | |
|---|---|---|
| AU | 2003247409 | 7/2008 |
| AU | 2004270174 | 11/2010 |

(Continued)

OTHER PUBLICATIONS

Nyholm, Dag, "Phamacotherapy for Parkinson's Disease—Observations and Innovations," Comprehensive Summaries of Uppsala Dissertations from the Faculty of Medicine 1236, 2003.
Lewitt, Peter et al., "New Developments in Levodopa Therapy," Neurology, 62(1 suppl. 1):S9-S16, 2004.
Han, Chien-Hsuan, Declaration Under 37 U.S.C. §1.132, Oct. 14, 2004.
Hiroshi, Nagayama, et al., "The Effect of Ascorbic Acid on the Pharmacokinetics of Levodopa in Elderly Patients with Parkinson's Disease," Clinical Neuropharmacology, 2004, 27:270-3.
Fincher, Julian H., "Particle Size of Drugs and its Relationship to Absorption and Activity," Journal of Pharmaceutical Sciences, 1968, 57:1825-35.
Actavis Laboratories FL, Inc., Notification of Certification for U.S. Pat. Nos. 9,089,607 and 9,089,608 Pursuant to § 505(j)(2)(B)(ii) of the Federal Food, Drug, and Cosmetic Act, Aug. 13, 2015.

(Continued)

*Primary Examiner* — Susan T Tran
(74) *Attorney, Agent, or Firm* — Florek & Endres PLLC

(57) ABSTRACT

The invention provides a controlled release oral solid formulation comprising (a) a controlled release component comprising core comprising levodopa and/or an ester of levodopa or salts thereof, wherein the core is coated with a layer of a muco-adhesive polymer and externally coated with a layer of an enteric coated polymer; and (b) a decarboxylase inhibitor component.

22 Claims, 7 Drawing Sheets

(56) References Cited

U.S. PATENT DOCUMENTS

| | | |
|---|---|---|
| 5,652,271 A | 7/1997 | Harris et al. |
| 5,681,583 A | 10/1997 | Conte et al. |
| 5,738,874 A | 4/1998 | Conte et al. |
| 5,773,031 A | 6/1998 | Shah et al. |
| 5,780,057 A | 7/1998 | Conte et al. |
| 5,840,756 A | 11/1998 | Cohen |
| 5,945,424 A | 8/1999 | Schmidt |
| 6,024,981 A | 2/2000 | Khankari et al. |
| 6,027,748 A | 2/2000 | Conte et al. |
| 6,126,969 A | 10/2000 | Shah et al. |
| 6,183,778 B1 | 2/2001 | Conte et al. |
| 6,194,000 B1 | 2/2001 | Smith et al. |
| 6,221,392 B1 | 4/2001 | Khankari et al. |
| 6,238,699 B1 | 5/2001 | Rubin |
| 6,294,200 B1 | 9/2001 | Conte et al. |
| 6,309,666 B1 | 10/2001 | Hatano |
| 6,372,252 B1 | 4/2002 | Blume et al. |
| 6,372,254 B1 | 4/2002 | Ting et al. |
| 6,376,545 B1 | 4/2002 | Levin |
| 6,500,867 B1 | 12/2002 | Virkki et al. |
| 6,531,153 B2 | 3/2003 | Seth |
| 6,602,521 B1 | 8/2003 | Ting et al. |
| 6,627,223 B2 | 9/2003 | Percel et al. |
| 6,630,162 B1 | 10/2003 | Nilvebrant et al. |
| 6,723,348 B2 | 4/2004 | Faham et al. |
| 6,730,321 B2 | 5/2004 | Ting et al. |
| 6,733,781 B2 | 5/2004 | Abu-Izza et al. |
| 6,793,936 B2 | 9/2004 | Devane et al. |
| 6,797,732 B2 | 9/2004 | Virkki et al. |
| 6,811,794 B2 | 11/2004 | Burnside et al. |
| 7,048,945 B2 | 5/2006 | Percel et al. |
| 7,094,427 B2 | 8/2006 | Han et al. |
| 8,377,474 B2 | 2/2013 | Hsu et al. |
| 8,557,283 B2 | 10/2013 | Hsu et al. |
| 9,089,607 B2 | 7/2015 | Hsu et al. |
| 9,089,608 B2 | 7/2015 | Hsu et al. |
| 9,463,246 B2 | 10/2016 | Hsu et al. |
| 2001/0046964 A1 | 11/2001 | Percel et al. |
| 2002/0155154 A1 | 10/2002 | Wong et al. |
| 2002/0192290 A1 | 12/2002 | Seth |
| 2003/0147957 A1 | 8/2003 | Licht et al. |
| 2003/0152628 A1 | 8/2003 | Licht et al. |
| 2003/0203028 A1 | 10/2003 | Ting et al. |
| 2003/0224045 A1 | 12/2003 | Han et al. |
| 2003/0228360 A1 | 12/2003 | Han et al. |
| 2004/0028613 A1 | 2/2004 | Quay |
| 2004/0166159 A1 | 8/2004 | Han et al. |
| 2005/0070608 A1 | 3/2005 | Remenar et al. |
| 2005/0147670 A1 | 7/2005 | Hsu et al. |
| 2005/0203185 A1 | 9/2005 | Remenar et al. |
| 2006/0013875 A1 | 1/2006 | Hsu et al. |
| 2006/0018965 A1 | 1/2006 | Moodley et al. |
| 2006/0045865 A1* | 3/2006 | Jacob .................. A61K 9/006 424/78.27 |
| 2006/0057197 A1 | 3/2006 | Han et al. |
| 2007/0003621 A1 | 1/2007 | Nangia et al. |
| 2007/0148238 A1 | 6/2007 | Nangia et al. |
| 2007/0190145 A1 | 8/2007 | Venkatesh et al. |
| 2007/0275060 A1 | 11/2007 | Befumo et al. |
| 2008/0299204 A1 | 12/2008 | Nangia et al. |
| 2009/0004229 A1 | 1/2009 | Pastini et al. |
| 2010/0298268 A1* | 11/2010 | Hsu .................. A61K 9/1652 514/64 |
| 2011/0111024 A1 | 5/2011 | Mao et al. |
| 2012/0177731 A1 | 7/2012 | Hsu et al. |
| 2013/0195973 A1 | 8/2013 | Gupta et al. |
| 2016/0287523 A1 | 10/2016 | Hsu et al. |

FOREIGN PATENT DOCUMENTS

| | | |
|---|---|---|
| EP | 0253490 | 1/1988 |
| EP | 0313845 | 5/1989 |
| EP | 0393572 | 10/1990 |
| EP | 0320051 | 11/1992 |
| EP | 1262198 | 12/2004 |
| EP | 1416920 | 1/2007 |
| EP | 1670450 | 1/2011 |
| EP | 2508174 A1 | 10/2012 |
| JP | 2005528430 | 9/2005 |
| JP | 2007504143 | 3/2007 |
| JP | 2011507956 | 3/2011 |
| JP | 2011518418 | 11/2011 |
| JP | 2015187178 | 10/2015 |
| KR | 1020137024633 | 11/2013 |
| KR | 1020107016189 | 11/2014 |
| KR | 1020157032127 | 6/2017 |
| MX | 332396 | 7/2015 |
| NZ | 586870 | 10/2012 |
| WO | 1995001781 | 1/1995 |
| WO | 1999004765 | 2/1999 |
| WO | 99/17745 | 4/1999 |
| WO | 1999017745 | 4/1999 |
| WO | 1999051209 | 10/1999 |
| WO | 2000015197 | 3/2000 |
| WO | 2000018447 | 4/2000 |
| WO | 2002000213 | 1/2002 |
| WO | 2003000018 | 1/2003 |
| WO | 2003005967 | 1/2003 |
| WO | 2005023185 | 3/2005 |
| WO | 2005099678 | 10/2005 |
| WO | 2006026556 | 3/2006 |
| WO | 2007002516 | 1/2007 |
| WO | 2007002518 | 1/2007 |
| WO | 2007/022956 | 5/2007 |
| WO | 2007/090091 | 11/2007 |
| WO | 2012/136816 | 10/2012 |
| WO | 2012/136819 | 10/2012 |
| WO | 2015/054302 | 4/2015 |

OTHER PUBLICATIONS

Actavis Laboratories FL, Inc., Notification of Certification for U.S. Pat. Nos. 8,377,474; 8,557,283; 8,454,998; and 7,094,427 Pursuant to § 505(j)(2)(B)(ii) of the Federal Food, Drug, and Cosmetic Act, Aug. 4, 2015.

Impax Laboratories, Inc., Complaint against Actavis Laboratories FL, Inc. and Actavis Pharma Inc., Action for Patent Infringement under the Food and Drug Laws and Patent Laws of the United States, Sep. 17, 2015.

Mark, Margery H., et al., Controlled-Release Carbidopa-Levodopa (Sinemet) in Combination with Standard Sinimet in Advanced Parkinson's Disease, 19 Annals Clinical Laboratory Sci. 101 (1989).

Hoffman, et al., Pharmacokinetic and Pharmacodynamic Aspects of Gastroretentive Dosage Forms, Intl. J. of Pharmaceutics, 227, 2004.

Yeh, K.C., et al., Pharmacokinetics and Bioavailability of Sinimet CR; A Summary of Human Studies, 39 Neurology 25 (Supp. 2 1989).

Cedarbaum, Jesse M., et al., A Pharmacokinetic and Pharmacodynamic Comparison of Sinimet CR (50/200) and Standard Sinimet (25/100), 39 Neurology 38 (Supp. 2 1989).

Grahnen, A, et al., Comparative Multiple-Dose Pharmacokinetics of Controlled-Release Levodopa Products, 32 European Neurology 343 (1992).

Young, Rosabel, Update on Parkinson's Diease, 59 AM. Family Physician 2155 (1999).

Sasahara, K., et al., Dosage Form Design for Improvement of Bioavailability of Levodopa II: Bioavailability of Marketed Levodopa Preparations in Dogs and Parkinsonian Patients, Journal of Pharmaceutical Sciences, 69(3), 1980.

Klausner, et al., Novel Levodopa Gastroretentive Dosage Form: in-vivo Evaluation in Dogs, J. Controlled Release, 88, 2003.

Klausner, et al., Novel Gastroretentive Dosage Form: Evaluation of Gastroretentivity and its Effect on Levodopa Absorption in Humans, Pharm. Res., 20(9), 2003.

Notification pursuant to Section 505 (j) (2) (B) (iv) of the Federal Food Drug and Cosmetic Act, Feb. 14, 2017.

Akhgari et al. "Statistical Optimization of Indomethacin Pellets Coated with Ph-Dependent Methacrylic Polymers for Possible Colonic Drug Delivery." International Journal of Pharmaceutics, 305:22-30 (2005).

(56) References Cited

OTHER PUBLICATIONS

Badawy, Sherif I., and Hussain, Munir A., "Microenvironmental pH Modulation in Solid Dosage Forms." Journal of Pharmaceutical Sciences, vol. 96, No. 5, 948-59 (2007).
Bredenberg et al., "An Automatic Dose Dispenser for Microtablets—A New Concept for Individual Dosage of Drugs in Tablet Form." International Journal Pharmaceutics, 261:137-46 (2003).
Cedarbaum, Jesse M., "Clinical Pharmacokinetics of Anti-Parkinsonian Drugs." Clinical Pharmacokinetics, 13(3): 141-78 (1987).
Cedarbaum, Jesse M., "The promise and Limitations of Controlled-Release Oral Levodopa Administration." Clinical Neuropharmacology, 12(3): 147-66 (1989).
Chourasia, M.K., and Jain, S.K. "Pharmaceutical Approaches to Colon Targeted Drug Delivery Systems." Journal of Pharmacy and Pharmaceutical Sciences, 6(1); 33-66 (2003), http://ualberta.ca/~csps/JPPS6(1)/S.Chourasia/colon.htm.
Cole et al., "Enteric Coated HPMC Capsules Designed to Achieve Intestinal Targeting." International Journal Pharmaceutics, 231(1): 83-95 (2002).
Contin et al., "Pharmacokinetic Optimisation in the Treatment of Parkinson's Disease." Clinical Pharmacokinetics, 30(6):463-81 (1996).
Crevoisier et al., "Bioavailability of L-Dopa after Madopar HBS Administration in Healthy Volunteers." European Neurology, 27 (Suppl. 1): 36-46 (1987).
Crevoisier et al., "Comparative Single- and Multiple-Dose Pharmacokinetics of Levodopa and 3-O-Methyldopa Following a New Dual-Release and a Conventional Slow-Release Formulation of Levodopa and Benserazide in Healthy Volunteers." European Neurology, 49(1): 39-44 (2003).
Dave et al., "Expression of Heteromeric Amino Acid Transporters along the Murine Intestine." J Physiol 558.2, 597-610 (2004).
Dingemanse, et al. "Pharmacokinetic Studies with a Dual-Release Formulation of Levodopa, a Novel Principle in the Treatment of Parkinson's Disease." European Neurology, 39(2): 119-24 (1998).
Espinoza et al., "Influence of Admixed Citric Acid on the Release Profile of Pelanserin Hydrochloride from HPMC Matrix Tablets." International Journal Pharmaceutics, 201(2): 165-73 (2000).
Gomes, P. and Soares-Da-Silva, P., "Na+ Independent Transporters, LAT-2 and B0,+, Exchange L-DOPA with Neutral and Basic Amino Acids in Two Clonal Renal Cell Lines." Journal Membrane Biology, 186(2): 63-80 (2002).
Gomes, P. and Soares-Da-Silva, P., "L-DOPA Transport Properties in an Immortalised Cell Line of Rat Capillary Cerebral Endothelial Cells, RBE 4." Brain Research, 829 (1-2): 143-50 (1999).
Goole et al., "Developmental and Evaluation of New Multiple-Unit Levodopa Sustained-Release Floating Dosage Forms." International Journal of Pharmaceutics, 334(1-2): 35-41 (2007).
Goole et al., "Evaluation and Floating Enhancement of Levodopa Sustained Release Floating Minitablets Coated with Insoluble Acrylic Polymer." Drug Development and Industrial Pharmacy, 34(8): 827-33 (2008).
Guthmann et al., "Development of a Multiple Unit Pellet Formulation for a Weakly Basic Drug." Drug Development and Industrial Pharmacy, 33(3): 341-49 (2007).
Horter, D., and Dressman, J.B., "Influence of Physicochemical Properties on Dissolution of Drugs in the Gastrointenstinal Tract." Advance Drug Delivery Reviews, 46(1-3): 75-87 (2001).
Iida, et al., "Improvement of Intestinal Absorption of P-glycoprotein Substrate by Dtartaric Acid." Drug Metabolism and Pharmacokinetics, 21(5): 424-8 (2006).
Jenner, Peter, "Avoidance of Dyskinesia: Preclinical Evidence for Continuous Dopaminergic Stimulation." Neurology, 62 (Suppl. 1): S47-55 (2004).
Kendall, Richard and Basit, Abdul W., "The Role of Polymers in Solid Oral Dosage Forms." Polymers in Drug Delivery, 35-48 (Ijeoma F. Uchebbo and Andres G. Schatzlein eds., 2006).
Khor, Soo-Pean and Hsu, Ann, "The Pharmacokinetics and Pharmacodynamics of Levodopa in the Treatment of Parkinson's Disease." Current Clinical Pharmacology, 2(3): 234-43 (2007).

Knop, Klaus and Kleinebudde, Peter, "Pharmaceutical Pellets." ExAct, No. 15 (Nov. 2005).
Kranz, et al., "Development of a Single Unit Extended Release Formulation for Zk 811 752, a Weakly Basic Drug." European Journal of Pharmaceutics Sciences, 26(1): 47-53 (2005).
Lee, A.J., "The On-Off Phenomenon." Journal of Neurology, Neurosurgery, and Psychiatry, Special Supplement 29-37 (1989).
Lewitt, Peter A., "Clinical Studies with and Pharmacokinetic Considerations of Sustained-Release Levodopa." Neurology, 42 (Suppl. 1): 29-32 (1992).
Lewitt, Peter A., "Levodopa Therapeutics: New Treatment Strategies." Neurology, 43 (Suppl. 6): S31-7 (1993).
Li et al., "Enteric-Coated Layered Double Hydroxides as a Controlled Release Drug Delivery System." International Journal of Pharmaceutics, 287(1-2): 89-95 (2004).
Lorenzo-Lamosa et al., "Design of Microencapsulated Chitosan Microspheres for Colonic Drug Delivery." Journal of Control Release, 52 (1-2): 109-18 (1998).
MacMahon et al., "A Comparison of the Effects of Controlled-Release Levodopa (Madopar CR) with Conventional Levodopa in late Parkinson's Disease." Journal of Neurology, Neurosurgery, and Psychiatry, 53(3): 220-23 (1990).
Malcolm et al., "Single-Dose Pharmacokinetics of Madopar HBS in Patients and Effect of Food and Antacid on the Absorption of Madopar HBS in Volunteers." European Neology, 27(Suppl. 1): 28-35 (1987).
Mylan Bioequivalence ANDA 75-091 (1998).
Nyholm, Dag and Aquilonius, Sten-Magnus, "Levodopa Infusion Therapy in Parkinson Disease: State of the Art in 2004." Clinical Neuropharmacology, 27(5): 245-56 (2004).
Nyholm, Dag, "Pharmacokinetic Optimisation in the Treatment of Parkinson's Disease: An Update." Clinical Pharmacokinetics, 45(2): 109-36 (2006).
Nyholm et al., "Optimizing Levodopa Pharmacokinetics: Intestinal Infusion Versus Oral Sustained-Release Tablets." Clinical Neuropharmacology, 26(3): 156-63 (2003).
Nykanen et al., "Citric Acid as Excipient in Multiple Unit Enteric-Coated Tablets for Targeting Drugs on the Colon." International Journal Pharmaceuticas, 229(1-2): 155-62 (2001).
Ogawa, Norio, "Factors Affecting Levodopa Effects in Parkinson's Disease." Acta Med Okayama, 54(3): 95-101 (2000).
Pinho et al., "Over Expression of Renal LAT1 and LAT2 and Enhanced LDOPA Update in SHR Immortalized Renal Proximal Tubular Cells." Kidney International, 66(1): 216-26 (2004).
Poewe et al., "Treatment of Motor Fluctuations in Parkinson's Disease with an Oral Sustained-Release Preparation of L-Dopa: Clinical and Pharmacokinetic Observations." Clinical Neuropharmacology, 9(5): 430-9 (1986).
Quinones et al., "The Dopamine Precursor L-Dihydroxyphenylalanine is Transported by the Amino Acid Transporters rBAT and LAT2 in Renal Cortex." American Journal of Physiology Renal Physiology, 287(1): F74-80 (2004).
Rao et al., "Parkinson's Disease: Diagnosis and Treatment." American Family Physician, 74(12): 2047-54 (2006).
Scattergood et al., "Comparative Study of Theoretical Versus Actual Weight Gain for a Surelease® Barrier Membrane on Coated Pellets." www.colorcon.com, mr/poster/SureSpheres/stud_comp_wt_gain_REV/Rev1.2009 (2004).
Seipe et al., "Strategies for the Design of Hydrophilic Matrix Tablets with Controlled Microenvironmental pH." International Journal of Pharmaceutics, 316 (1-2): 14-20 (2006).
Simon et al., "The Effects of a Normal Protein Diet on Levodopa Plasma Kinetics in Advanced Parkinson's Disease." Parkinsonism Related Disorders, 10(3): 137-42 (2004).
Sinemet® Label, 2002.
Tang et al., "Coating of Multiparticulates for Sustained Release." American Journal of Drug Delivery, 3(1): 17-28 (2005).
"Treatment of Early Parkinson's Disease." American Family Physician, 72(3): 497-500 (2005), http://aafp.org/afp/2005/0801/p497.html.
HSU Declaration, Aug. 2, 2005.
Bettini et al. "Influence of layer position on in vitro and in vivo release of levodopa methyl ester and carbidopa from three-layer

(56) References Cited

OTHER PUBLICATIONS matrix tablets," European Journal of Pharmaceutics and Biopharmaceutics, 2002, 53:227-32.

Deleu, et al., "Clinical and Pharmacokinetic comparison of oral and duodental delivery of levodopa/carbidopa in patients with Parkinson's disease with a fluctuating response to levodopa," European Journal of Clinical Pharmacology, 1991, 41:453-8.

Pahwa et al., Early morning akinesia in Parkinson's disease: Effect of standard carbidopa/levodopa and sustained-release carbidopa/levodopa, Neurology, 1996, 46: 1059-62.

Pahwa et al., "Comparison of Standard Carbidopa-Levodopa and Sustained-Release Carbidopa-Levodopa in Parkinson's Disease: Pharmacokinetic and Quality of Life Measures," Movement Disorders, 1997, 12:677-81.

Kurlan et al., "Duodenal and Gastric Delivery of Levodopa in Parkinsonism," Annals of Neurology, 1988, 23:589-95.

Kurlan et al., "Erratic gastic emptying of levodopa may cause 'random' fluctuations of parkinsonian mobility," Neurology, 1988, 38:419-21.

Baruzzi et al., "Influence of Meal Ingestion Time on Pharmacokinetics of Orally Administered Levodopa in Parkinsonian Patients," Clinical Neuropharmacolgy, 1987, 10:527-37.

\* cited by examiner

Figure 1 Schematic Configuration of Enteric-coated, Muco-adhesive Multi-particulates
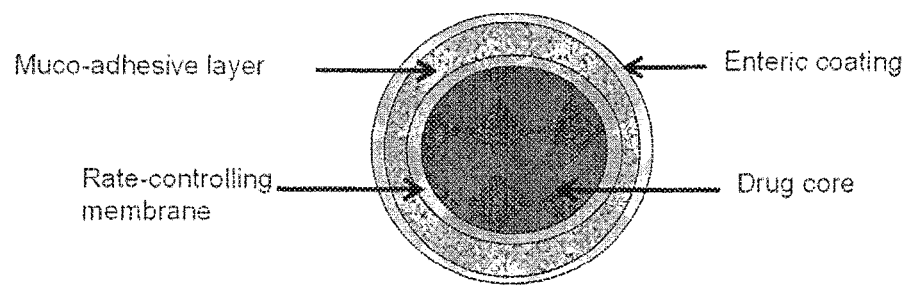

Figure 2: *In-vitro* Dissolution Profiles of IPX203 LDEE-S Formulations
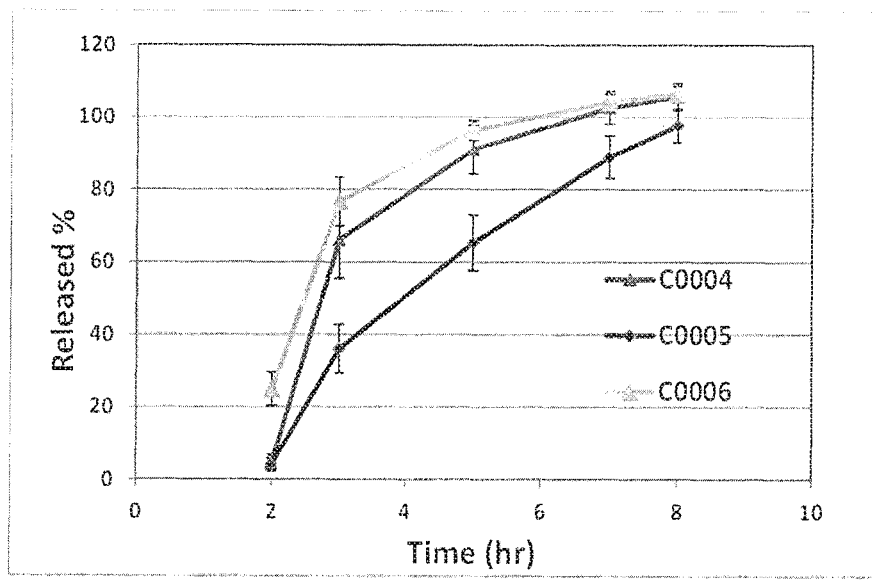
Note: Dissolution method is USP Apparatus 1 with basket speed of 75 rpm in pH 1.0 for 120 min then switch to pH 7 phosphate buffer.

Figure 3 LD Mean Plasma Concentration Profiles of IPX203 Capsules and Sinemet CR Tablet
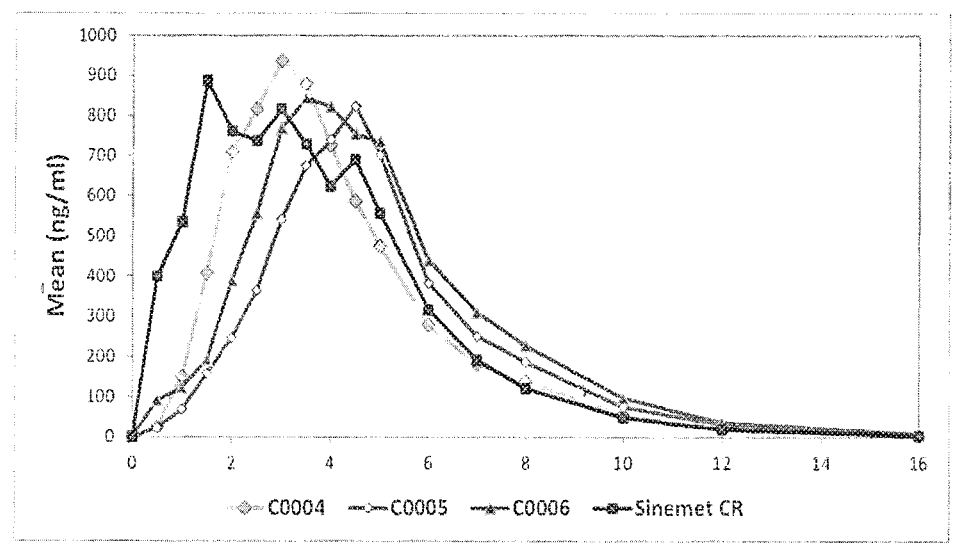

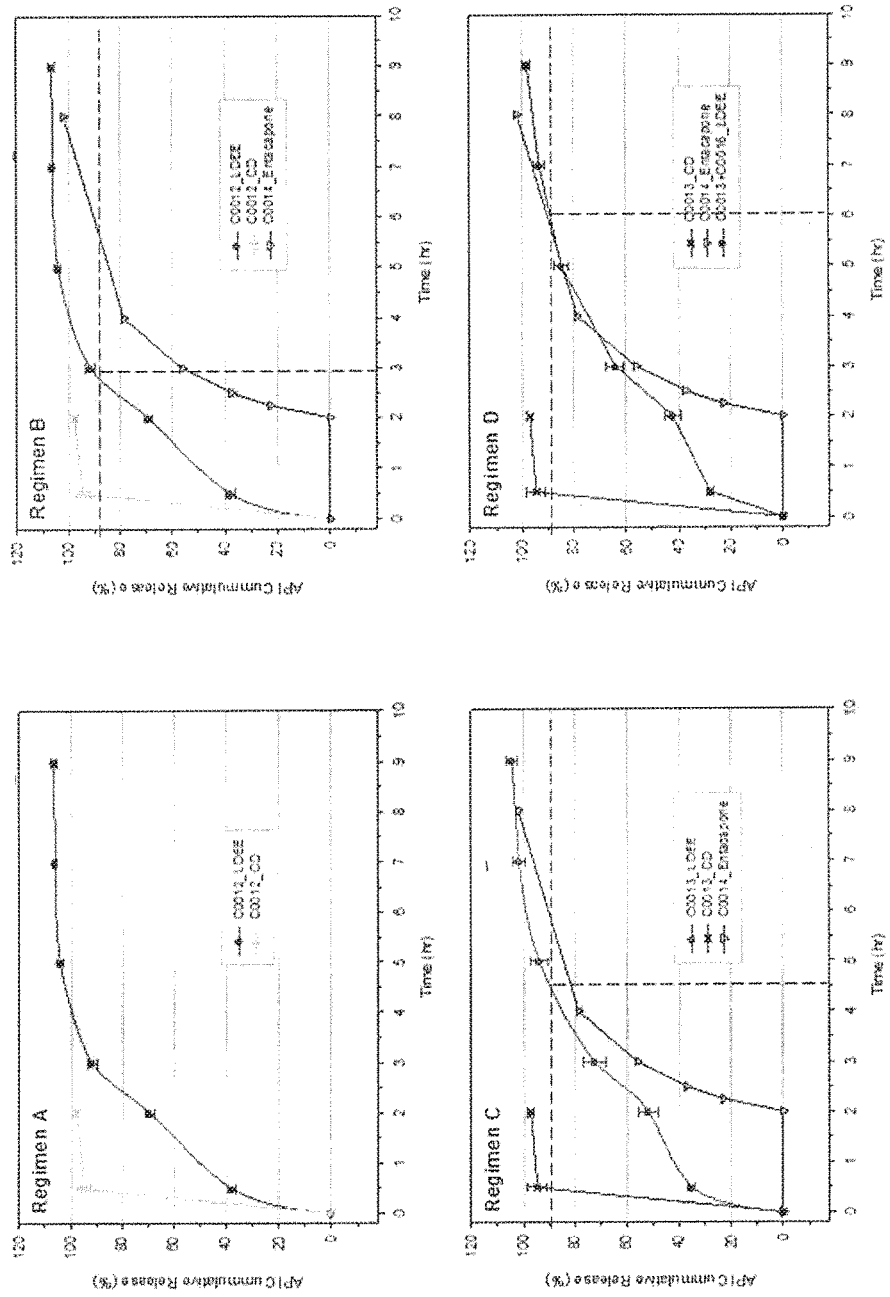

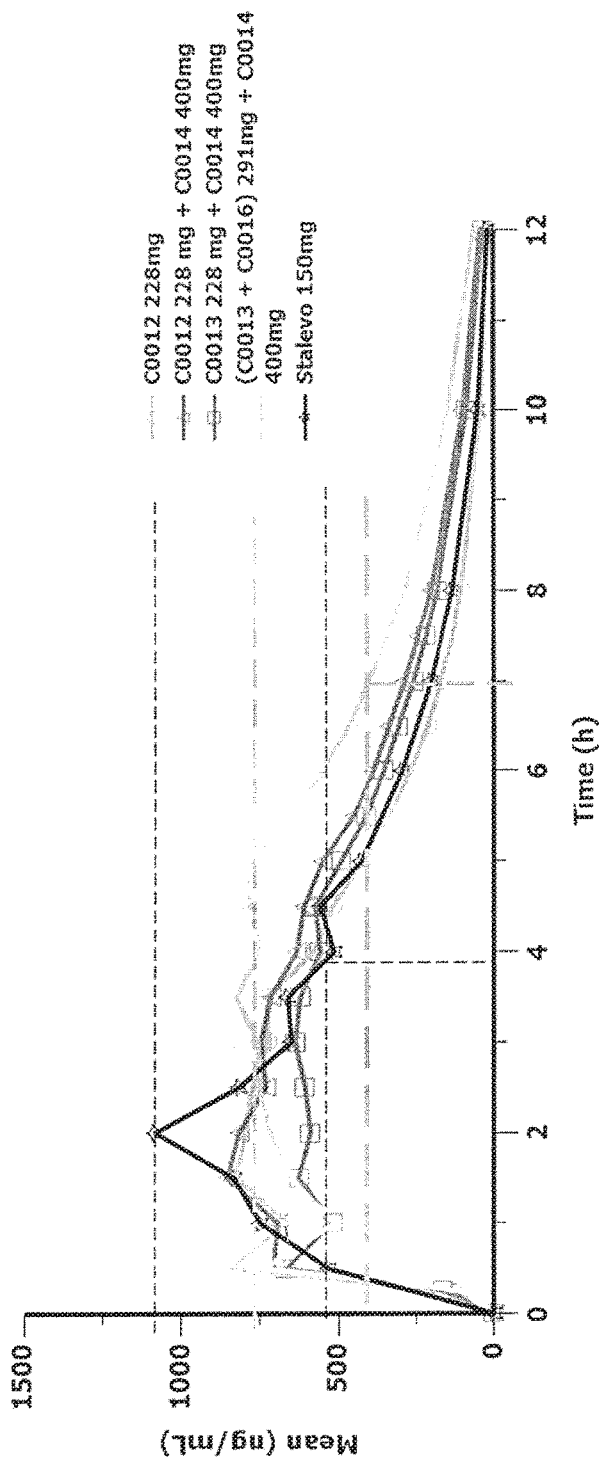

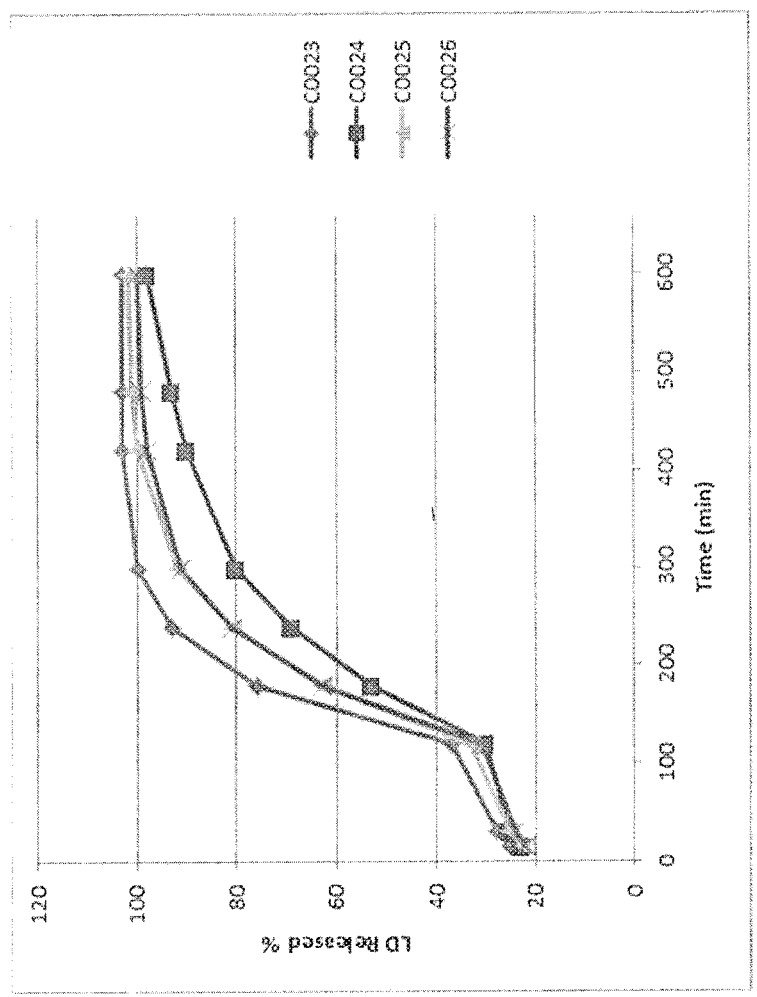
Figure 6: *In vitro* Release Profiles of IPX203-C0023, -C0024, -C0025 and -C0026 Formulations

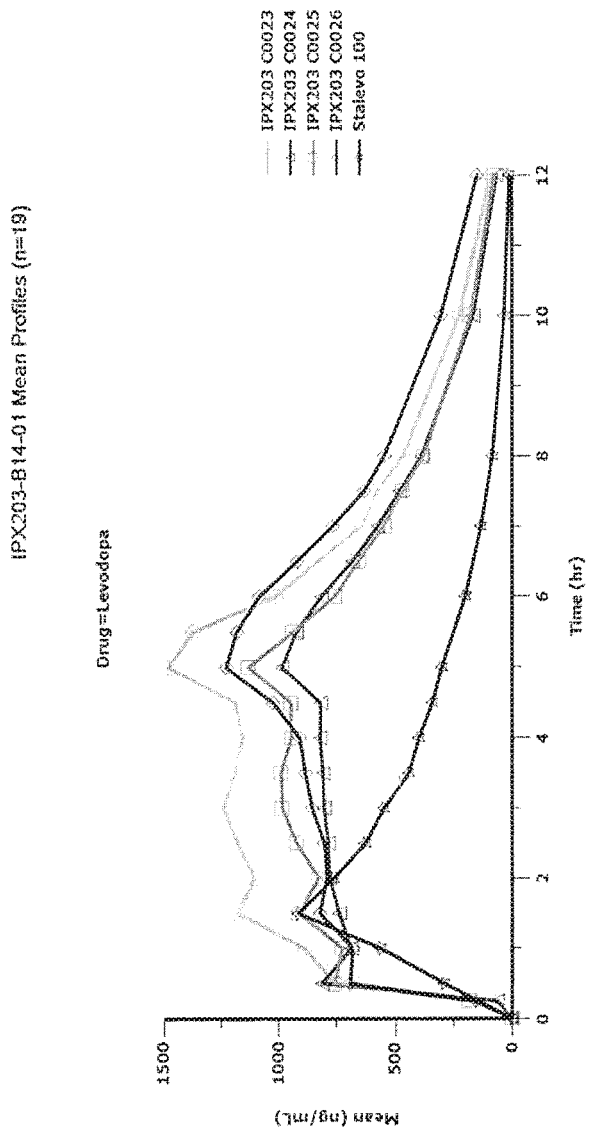

MUCO-ADHESIVE, CONTROLLED RELEASE FORMULATIONS OF LEVODOPA AND/OR ESTERS OF LEVODOPA AND USES THEREOF

This application is a U.S. National Stage filing under 35 U.S.C. § 371 of International Application No. PCT/US2014/059554, filed Oct. 7, 2014, which in turn claims priority to U.S. Provisional Application No. 61/887,762, filed Oct. 7, 2013, the contents of all of which are hereby incorporated by reference in their entireties into the present application.

Throughout this application various publications are referenced. The disclosures of these publications in their entireties are hereby incorporated by reference into this application in order to more fully describe the state of the art to which this invention pertains.

FIELD OF THE INVENTION

The present invention relates to controlled release pharmaceutical compositions of levodopa (LD) and esters of levodopa or salts thereof, formulated with a muco-adhesive polymer and an enteric coating polymer and, optionally, with a rate-controlling polymer, to yield enhanced drug delivery attributes. These formulations are useful for the treatment of conditions such as neurological diseases associated with reduced or impaired dopamine levels.

BACKGROUND OF THE INVENTION

Patients suffering from Parkinson's disease (PD) frequently have periods in which their mobility becomes difficult, often resulting in an inability to move. Abnormally low levels of dopamine, a neurotransmitter that affects mobility and control of the skeletal-muscular system, is commonly believed to be the main cause of these motor symptoms in PD patients. However, administration of dopamine is not effective to treat the motor symptoms of Parkinson's disease because dopamine does not cross the blood-brain barrier. To resolve this problem, PD patients are administered levodopa, the metabolic precursor of dopamine, but levodopa is not without its issues.

Over time patients treated with LD exhibit symptoms of "wearing off," where a single dose of levodopa no longer lasts as long as in the early days of levodopa therapy (usually 5-10 years after start of levodopa therapy). Such patients may develop motor fluctuations characterized by end-of-dose failure, peak dose dyskinesia, and akinesia. The advanced form of motor fluctuations (also commonly referred to as the 'on-off' phenomenon) is characterized by unpredictable swings from mobility to immobility. Although the causes of these motor fluctuations are not completely understood, advanced patients generally benefit from treatment regimens that produce steady plasma levels of LD, such as through intestinal infusion of LD as such delivery method may mimic normally tonic endogenous dopamine. However, intestinal infusion of LD is restrictive, invasive and cumbersome. Oral delivery of LD is preferred, but plasma concentration levels remain difficult to control via oral delivery.

Combinations of levodopa (LD) and a decarboxylase inhibitor (typically carbidopa (CD)) to treat Parkinson's disease (PD) are known in the pharmaceutical arts. Currently, several formulations containing a combination of LD and CD are commercially available, e.g., SINEMET®, SINEMET® CR, STALEVO®, PARCOPA®, and their corresponding generic products. In addition, a decarboxylase inhibitor approved for use outside of the United States, is benserazide, which may be given in combination with levodopa.

Nonetheless, a need remains for an oral LD formulation that provides steadier plasma concentrations of LD with minimal 'peak-to-trough' fluctuations during daily dosing and that yields a longer duration-of-effect than the commercially available oral dosage forms of LD. In addition, it is desirable for an oral LD formulation to provide therapeutic blood levels of LD quickly, thereby providing a rapid "on" to a PD patient in need thereof.

SUMMARY OF THE INVENTION

The current invention provides controlled release/extended absorption oral dosage forms comprising levodopa and/or ester of levodopa or salts thereof for treatment of Parkinson's disease and dopamine deficiency disorders. More specifically, in some embodiments, the dosage form comprises two types of components, the first component is an immediate release levodopa and/or its ester or salts thereof, and the second component comprises a core containing levodopa and/or ester of levodopa or salts thereof coated with a muco-adhesive polymer and externally coated with an enteric coating polymer, optionally, with a rate-controlling polymer undercoating the muco-adhesive polymer. The second component is essential to provide extended absorption, thereby providing prolonged and steady therapeutic coverage. The dosage form may comprise additionally a decarboxylase inhibitor, such as carbidopa.

BRIEF DESCRIPTION OF THE FIGURES

FIG. 1 shows the schematic configuration of the enteric-coated, muco-adhesive controlled release multi-particulates of this invention.

FIG. 2 is a line graph showing the in vitro dissolution profiles of IPX203 multi-particulate formulations IPX203-C0004, IPX203-C0005 and IPX203-C0006.

FIG. 3 shows the plasma profile for IPX203 multi-particulate formulations IPX203-C0004, IPX203-C0005 and IPX203-C0006 in comparison with Sinemet® CR.

FIG. 4 are line graphs showing in vitro release profiles of test regimens A-D for IPX203-B13-01.

FIG. 5 is a line graph showing in vivo levodopa plasma profiles of IPX203 formulations that provide plasma profiles with levodopa levels maintained at or greater than ½ Cmax longer than about 6 hours under fasted conditions.

FIG. 6 shows in vitro release profiles of IPX203-C0023, -C0024, -C0025 and -C0026 formulations.

FIG. 7 shows in vivo levodopa plasma profiles for the formulations tested in IPX203-B14-01 PK study under fasted conditions.

DETAILED DESCRIPTION OF THE INVENTION

Unless defined otherwise, all technical and scientific terms used herein have the same meaning as commonly understood by one of ordinary skill in the art to which the present disclosure belongs. As used herein the following terms have the following meanings:

It must be noted that as used herein and in the appended claims, the singular forms "a," "an," and "the" include plural referents unless the context clearly dictates otherwise. Thus, for example, reference to "a formulation" includes a plurality of compounds.

As used herein, the term "about" when used before a numerical designation, e.g., temperature, time, amount, concentration, and such other, including a range, indicates approximations which may vary by (+) or (−) 10%, 5% or 1%.

Compositions of the Invention

The invention provides controlled release oral solid formulations of levodopa and/or an ester of levodopa or a salt thereof providing a relatively steady levodopa plasma or serum concentration profile over a prolonged period of time and enhancing absorption of the active agents in the gastrointestinal tract of a subject. Without being limited by any one theory, it is believed that the polymer layers of the controlled release components of the present invention operate as follows. The outer enteric coat delays release of the active agents until the dosage form has passed through the stomach and into the small intestine. In the small intestine, the muco-adhesive polymer facilitates adhesion to the intestinal mucosa, delaying passage of the dosage form through the intestine. It is desirable to retain the dosage form within the small intestine where levodopa is absorbed most efficiently. In preferred embodiments, the third rate-controlling polymer further slows the release of active agent from the dosage form, thereby further extending the release and absorption of levodopa. Preferred formulations include an immediate release component to provide fast levodopa release and absorption, which is important for PD patients in need of a fast "on." As a result, formulations of the present invention can provide levodopa plasma levels that rise quickly and extend for a prolonged period of time.

Decarboxylase inhibitors such as carbidopa are often provided with levodopa formulations in order to inhibit decarboxylation of levodopa, thereby increasing the levodopa bioavailability. In the formulations of the present invention, a decarboxylase inhibitor may be included in both the immediate release component and the controlled release component. Preferably, the decarboxylase inhibitor is carbidopa and is included only in the immediate release component.

In one embodiment of the invention, the controlled release oral solid formulation contains (1) a controlled release component comprising a levodopa and/or an ester of levodopa or salts thereof and (2) an immediate release component comprising levodopa and/or an ester of levodopa or salts thereof and a decarboxylase inhibitor. The immediate release component may be formulated as a mini-tablet, bead or granule. The controlled release component comprises a core containing levodopa and/or an ester of levodopa or salts thereof coated with a layer of a muco-adhesive polymer and further coated with an outer layer of an enteric coating polymer. Preferably, the drug-containing core is coated with a further rate-controlling polymer, which undercoats the muco-adhesive polymer layer. In a preferred embodiment, the immediate release component is in the form of a granule.

In another embodiment of the invention, the controlled release oral solid formulation contains (1) a controlled release component comprising a levodopa and/or an ester of levodopa or salts thereof, and (2) a decarboxylase inhibitor component. The decarboxylase inhibitor component may be formulated as a mini-tablet, bead or granule. In this embodiment, the controlled release component comprises a drug-containing core coated with a layer of a muco-adhesive polymer and further coated with an outer layer of an enteric coating polymer. Preferably, the drug-containing core is coated with a further rate-controlling polymer that undercoats the muco-adhesive polymer layer. Preferably, the decarboxylase inhibitor is carbidopa. The controlled release component may comprise drug-containing cores containing both levodopa and/or an ester of levodopa or a salt thereof and a decarboxylase inhibitor, or the levodopa and/or ester of levodopa or salt thereof may be in separate controlled release components from that containing the decarboxylase inhibitor. In one embodiment of the invention, the controlled release component comprises a levodopa-containing core free of a decarboxylase inhibitor such as carbidopa. Preferably, the formulation further comprises an immediate release component comprising levodopa and/or an ester of levodopa or a salt thereof and a decarboxylase inhibitor.

In a preferred embodiment of the invention, the controlled release oral solid formulation contains (1) a controlled release component comprising levodopa and (2) an immediate release component comprising levodopa and carbidopa. In this embodiment, the controlled release component comprises a drug-containing core coated with a first layer of a rate-controlling polymer, a second layer of muco-adhesive polymer and further coated with an outer third layer of an enteric coating polymer (see, e.g., FIG. 1).

In accordance with the practice of the invention, the formulations of the invention may be obtained by a granulation process, including, but not limited to, wet-granulation, fluid bed granulation or dry granulation, as is well-known in the pharmaceutical arts. The controlled release components and/or the immediate release components may further contain a lubricant, such as talc.

In an embodiment of the invention, the controlled release and/or immediate release components are multiparticulates that are encapsulated. The multiparticulates may be in a form that can be sprinkled directly onto food or liquids for easy ingestion.

The active agents, such as decarboxylase inhibitor, levodopa and/or levodopa ethyl ester, may be combined and dispersed throughout the drug-containing core. In another embodiment, the active agents may be present in the center of the drug-containing core or layered on a sugar sphere.

In an embodiment of the invention, the controlled release oral solid formulation of levodopa or ester of levodopa or salts thereof may comprise two controlled release components that release levodopa or ester of levodopa or salts thereof at different rates.

In this embodiment, the controlled release oral solid formulation of levodopa or ester of levodopa or salts thereof may comprise two controlled release components differing in type, number, thickness and/or composition of coating with a rate-controlling polymer, a muco-adhesive polymer and an enteric-coating polymer.

Examples of levodopa include but are not limited to levodopa, L-DOPA, L-3,4-dihydroxyphenylalanine, and (S)-2-amino-3-(3,4-dihydroxyphenyl)propanoic acid.

An example of a decarboxylase inhibitor includes, but is not limited to, carbidopa. Additional decarboxylase inhibitors include alpha methyldopa, benserazide (Ro4-4602), and alpha-difluoromethyl-DOPA (DFMD) or salts thereof. In a preferred embodiment, the decarboxylase inhibitor is carbidopa.

An example of an ester of levodopa is a levodopa ethyl ester (LDEE; ethyl (2S)-2-amino-3-(3,4-dihydroxyphenyl)propanoate; CAS Number: 37178-37-3) and having the structure:

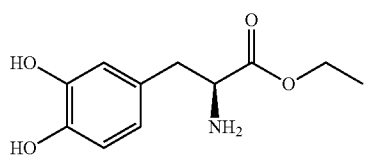 [SMILES: CCOC(=O)[C@@H](N)Cc1ccc(O)c(O)c1]

(levodopa ethyl ester, CAS Number 37178-37-3).

Additional examples of esters of levodopa include, but are not limited to:

levodopa butyl ester (butyl (2S)-2-amino-3-(3,4-dihydroxyphenyl)propanoate; CAS Number: 39638-52-3) having the structure:

levodopa propyl ester, levodopa propyl ester (propyl (2S)-2-amino-3-(3,4-dihydroxyphenyl)propanoate; CAS Number: 39638-51-2) having the structure:

and levodopa methyl ester (methyl (2S)-2-amino-3-(3,4-dihydroxyphenyl)propanoate; CAS Number: 7101-51-1), having the structure:

The ester of levodopa may be a salt, including, for example, a hydrated salt. The salt of levodopa ester may comprise, but is not limited to, any of an octonoate salt, myristate salt, succinate salt, succinate dihydrate salt, fumarate salt, fumarate dihydrate salt, mesylate salt, tartrate salt, and hydrochlorate salt.

For example, the succinate salt of an ester of levodopa or the succinate dihydrate salt may be a levodopa ethyl ester succinate (LDEE-S) or levodopa ethyl ester succinate dihydrate (LDEE-S-dihydrate or LDEE-S(d)).

As used herein, "levodopa equivalence" or "LD equivalence" means that amount of levodopa ester or salts thereof that contain equivalent amounts of levodopa, based on weight equivalence. For example, based on the molecular weights, 306 mg of levodopa ethyl ester succinate-dihydrate (LDEE-S-dihydrate) is equivalent to 228 mg of levodopa ethyl ester (LDEE) and to 200 mg levodopa (LD).

Muco-adhesive polymers may be homogenous, i.e., a single type of polymer, or may comprise multiple types of muco-adhesive polymers. Muco-adhesive polymers may possess certain characteristics such as being hydrophilic, hydrophobic, cationic, anionic and/or biocompatible and include multiple hydrogen bonding groups, hydrophobic surfaces, positively charged groups and/or negatively charged groups for adhesion to a mucosal surface so that the presence of active agent, such as levodopa, can be prolonged at the site of absorption and increase bioavailability. Further, the muco-adhesive polymer may be natural, synthetic or from a biological source. Further still, the muco-adhesive polymer may be composed of a single polymer or a combination of two or more different polymers. In one embodiment, the polymers may range in size from 10,000 daltons to 1,000,000 daltons and more preferably 20,000 daltons to 200,000 daltons.

An example of a muco-adhesive polymer includes, but is not limited to, a basic methacrylate copolymer, such as an amino methacrylate copolymer. A preferred example of a methacrylate copolymer is a basic butylated methacrylate copolymer, an amino methacrylate copolymer, or aminoalkyl methacrylate copolymer, such as Eudragit® E100

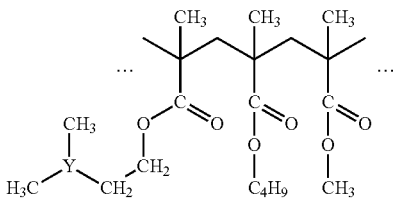

(poly(butyl methacrylate-co-(2-dimethylaminoethyl) methacrylate-co-methyl methacrylate) 1:2:1; CAS number: 24938-16-7; Evonik Industries). EUDRAGIT® E100 is a cationic copolymer based on dimethylaminoethyl methacrylate, butyl methacrylate, and methyl methacrylate with a ratio of 2:1:1. The monomers are randomly distributed along the copolymer chain. In a preferred embodiment, the average molar weight of EUDRAGIT® E100 is approximately 150,000 g/mol.

Other examples of muco-adhesive polymer include, but are not limited to, a glyceride, steroidal detergent, polycarbophil (CAS Number 9003-97-8; Noveon® AA-1; Lubrizol Corp.), carbomer, cellulosics, chitosan

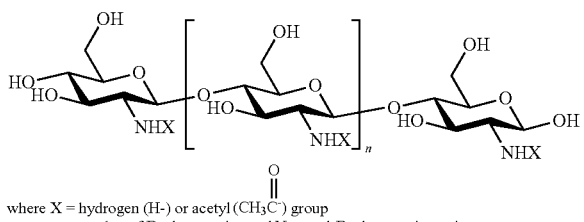

where X = hydrogen (H-) or acetyl (CH₃C⁻) group
n = number of D-glucosamine and N-acetyl-D-glucosamine units (CAS Number: 9012-76-4; Chitopharm® S with molecular weight range of 50,000 to 1,000,000 daltons), diethylaminodextran, diethylaminoethyldextran, polygalactosamine, polylysine, polyornithine, prolamine, polyimine, hyaluronic acid, sodium alginate, hydroxypropylcellulose (HPC), hydroxypropylmethylcellulose (HPMC), sodium carboxymethylcellulose (sodium CMC) and alginate (CAS Number: 9005-32-7) or combination thereof. Alginate is a homopolymer or heteropolymer composed of β-D-mannuronate (M) monomers, α-L-guluronate (G) monomers, or mixture of β-D-mannuronate and α-L-guluronate monomers

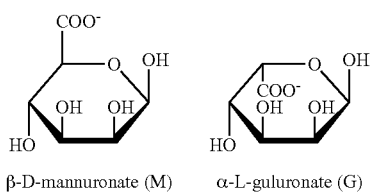

β-D-mannuronate (M)   α-L-guluronate (G)

linked through (1→4) or (1,4)-glycosidic bonds. The (1,4)-glycosidic linkages present in alginates are: β-D-mannuronate-(1,4)-β-D-mannuronate (MM), β-D-mannuronate-(1,4)-α-L-guluronate (MG), α-L-guluronate-(1,4)-β-D-mannuronate (GM) and α-L-guluronate-(1,4)-α-L-guluronate (GG), as can be seen below:

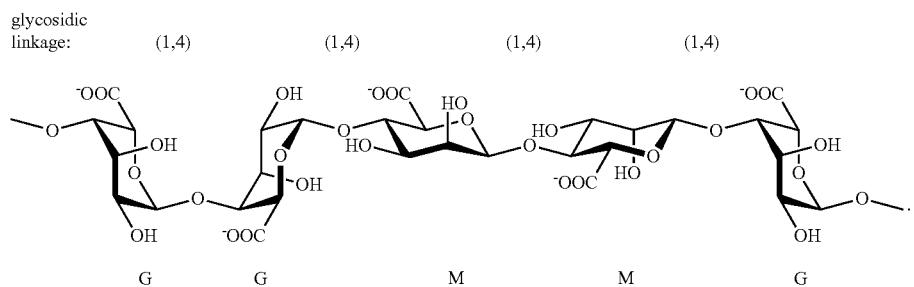

An alginate may be in the form of a polyanion or in the form of an acid, such as alginic acid. Further, alginate may be in the form of a salt of alginic acid, such as sodium alginate, potassium alginate, ammonium alginate, triethanolamine alginate, magnesium alginate or calcium alginate. Alternatively, alginate may be in the form of an ester of alginic acid such as propylene glycol alginate.

The muco-adhesive polymer may constitute 2%-50% of the mass of the controlled release component, preferably 3%-15% of the mass of the controlled release component, most preferably about 5.0%-7.5% of the mass of the controlled release component. Preferably, the muco-adhesive polymer is Eudragit E 100. The muco-adhesive polymer percentages of mass stated above are based on a multiparticulate with a bead size between 0.8 to 1.2 mm. If the bead size is larger or smaller than 0.8 to 1.2 mm, the skilled artisan will understand that the mass percentage described above should be adjusted accordingly.

Enteric coating polymers are known in the art. In general, enteric coating polymers are designed to prevent drug release from an oral solid dosage form in the low pH environment of the stomach, thereby delaying drug release until the dosage form reaches the small intestine. As such, the controlled release components of the invention have an in vitro release profile with minimal release of the active agent at pH 1.0. In the controlled release formulations of the invention, it is believed the outer enteric coating polymer layer provides an additional advantage in preventing agglomeration of the controlled release components. That is, the enteric coat polymer layer prevents the controlled release beads from sticking together in the low pH environment of the stomach.

The preferred enteric polymers are shellac (esters of aleurtic acid), cellulose acetate phthalate (CAP), poly(methacrylic acid-co-methyl methacrylate), poly(methacrylic acid-co-ethyl methacrylate), cellulose acetate trimellitate (CAT), poly(vinyl acetate phthalate) (PVAP), hydroxypropyl methylcellulose phthalate (HPMCP) and hydroxypropyl methylcellulose acetate succinates. The preferred enteric polymers release at a pH of greater than or equal to pH 5.5. Examples include Eudragit® L100 or Eudragit® L100-55. The enteric coating polymers may constitute 2-20% of the mass of the controlled release component, preferably 3-15%, most preferably 5-12%. The enteric-coated polymer percentages stated above are based on a multiparticulate bead size between 0.8-1.2 mm. If the bead size is smaller or larger, the skilled artisan will understand that the mass percentage described above should be adjusted accordingly.

The enteric coating polymer may comprise a methacrylic acid copolymer or multiple types of methacrylic acid copolymers. The methacrylic copolymer may comprise any of Eudragit® L 30 D-55

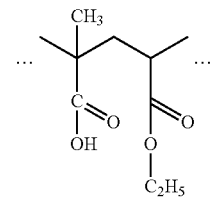

(poly(methacrylic acid-co-ethyl acrylate) 1:1; CAS Number 25212-88-8; Evonik Industries), Eudragit® L 100-55

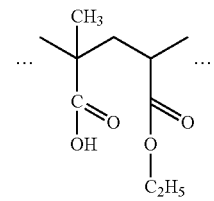

(poly(methacrylic acid-co-ethyl acrylate) 1:1; CAS Number 25212-88-8; Evonik Industries), Eudragit® L 100

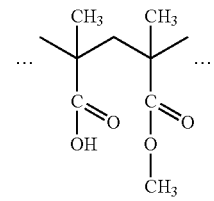

(poly(methacrylic acid-co-methyl methacrylate) 1:1; CAS Number 25086-15-1; Evonik Industries), Eudragit® L 12,5

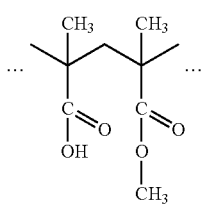

(poly(methacrylic acid-co-methyl methacrylate) 1:1; CAS Number 25086-15-1; Evonik Industries); Eudragit® S 100

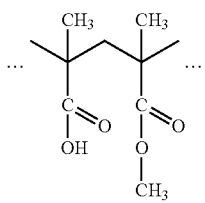

(poly(methacrylic acid-co-methyl methacrylate) 1:2; CAS Number 25086-15-1; Evonik Industries), Eudragit® S 12,5

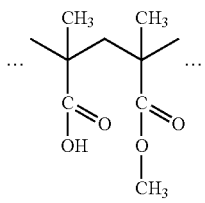

(poly(methacrylic acid-co-methyl methacrylate) 1:2; CAS Number 25086-15-1; Evonik Industries), and Eudragit® S 30 D

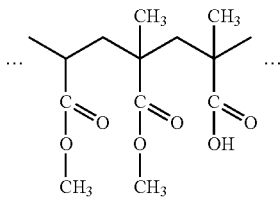

(poly(methyl acrylate-co-methyl methacrylate-co-methacrylic acid) 7:3:1; CAS Number 26936-24-3; Evonik Industries) or a combination thereof.

In a preferred embodiment of present invention, the controlled release component comprises a further rate-controlling polymer coat over the drug-containing core, undercoating the muco-adhesive polymer. Examples of rate-controlling polymers useful in the present invention include, but are not limited to, ethylcellulose, cellulose acetate, Eudragit® E, Eudragit® RS, Eudragit® RL, and Eudragit® NE, or mixtures thereof. Preferably, the rate-controlling polymers are not soluble in water at neutral pH. Preferably, the rate-controlling polymer is cellulose acetate. The rate-controlling polymer can also include a flux enhancer to adjust the release rate. Preferably, the flux enhancer is copovidone, PEG 3350, or low molecular weight HPMC.

Lubricants useful in pharmaceutical formulations are known in the art. Examples of a suitable lubricant include, but are not limited to, stearic acid, lauric acid, myristic acid, palmitic acid, fatty acid, magnesium stearate, calcium stearate, zinc stearate, sodium stearate, Stear-O-Wet®, sodium stearyl fumarate, salt of a fatty acid, metallic salt of fatty acid, glyceryl monostearate, glyceryl tribehenate, glyceryl dibehenate, Compritol® 888 ATO, glyceride ester, sorbitan monostearate, sucrose monopalmitate, sugar ester, fatty acid ester, talc, hydrated magnesium silicate, PEG 4000, boric acid, Carbowax (PEG) 4000/6000, sodium oleate, sodium benzoate, sodium acetate, sodium lauryl sulfate, magnesium lauryl sulfate, Sterotex, wax, or mixture thereof.

In accordance with the practice of the invention, a surfactant may be included, such as sodium lauryl sulfate. Other surfactants may be suitable and are well known in the art.

In an embodiment of the invention, the carbidopa and the levodopa or levodopa equivalence are present in the formulation of the invention in a weight ratio of about 1:1 to about 1:10, preferably about 1:4.

For example, useful amounts of levodopa or levodopa equivalence and carbidopa include: (a) 200 mg:31.25 mg; (b) 200 mg:50 mg; (c) 255.6 mg:50 mg; (d) 360 mg:50 mg; (e) 95 mg:23.75 mg; (f) 145 mg:36.25 mg; (g) 195 mg:48.75 mg; (h) 245 mg:61.25 mg; or (i) 390 mg:97.5 mg; with each value capable of varying by ±10%. Further examples include amounts of levodopa:carbidopa or levodopa equivalence: carbidopa as follows: (a) 95 mg:23.75 mg; (b) 145 mg:36.25 mg; (c) 195 mg:48.75 mg; or (d) 245 mg:61.25 mg; with each value capable of varying by ±10%.

In an embodiment of the invention, the immediate release component may comprise less levodopa or levodopa equivalence dosage than the controlled release component. For example, the ratio of levodopa or levodopa equivalence in the immediate release component to that in the controlled release component can be in the range of 0.15 to 0.65. For example, a ratio in weight of levodopa equivalence in the controlled release component:immediate release component is at least about 2:1, most preferably 3:1.

In one embodiment of the invention, the controlled release component is a bead having a size that passes through 12, 14, or 16 mesh but may be retained on 18, 24 or 25 mesh screens. Further, the bead may have a size that passes through 14 mesh but may be retained on 18 or 24 mesh screens.

The controlled release component will have an in vitro dissolution profile showing minimal release of the levodopa and/or ester of the levodopa or a salt thereof at pH 1.0 and extended release of the ester of levodopa or a salt thereof near neutral pH, for example at or near pH 7. For example, minimal release may entail less than 20% release of levodopa, preferably less than 10%, most preferably less than 5% using USP I dissolution method at agitation speed of 75 rpm in Simulated Gastric Fluid (pH 1.0, without enzyme) for 2 hrs. Further, extended release may involve release at over at least four and up to an additional 8 hours at or near pH 7, upon changing to Simulated Intestinal Fluid (pH 7.0, without enzyme) after first 2 hrs in Simulated Gastric Fluid (pH 1.0, without enzyme) using USP I dissolution method at agitation speed of 75 rpm. Further still, as used here, at or near pH 7 includes a pH at or about pH 6.5, 6.6, 6.7, 6.8 6.9, 7.1, 7.2, 7.3, 7.4, 7.5 or 7.6.

The levodopa and/or ester of levodopa or a salt thereof released from the controlled release component may produce an in vivo levodopa plasma profile (e.g., mean in vivo levodopa plasma profile) comprising a peak occurring not before about two hours after administration to a subject and provides at least three hour duration for levodopa plasma concentration above 50% the maximum value of the peak concentration (Cmax). In another embodiment, in the plasma profile, the peak occurs after about one and a half hours after administration to the subject and exhibits at least a four-hour duration for levodopa plasma concentration at or above 50% of Cmax. By way of example, the profile may be achieved under fasting conditions.

When the formulation of the invention comprises an immediate release component and a controlled release component, the in vivo levodopa plasma profile following administration of an oral dosage form of the formulation to a subject may comprise time of administration of an oral dosage form; a levodopa plasma concentration corresponding to Cmax occurring within about 6 hours or 7 hours after administration of the dosage form; a mean time to reach 50% of Cmax within one hour of administration, more preferably within 30 minutes. The time to 50% of Cmax is less than one hour and 50% Cmax is maintained for at least 5.0 hours. The time after administration of the dosage form when the maximum plasma concentration is reached (Tmax) is between 30 minutes and 7 hours. Preferably, the LD plasma level is maintained at or above 50% of Cmax for at least 5.5 hours, more preferably, for at least 6.0 hours, even more preferably, for at least 6.5 hours, and most preferably for at least 7.0 hours.

In one embodiment, the formulations of the invention may have a ratio of said Cmax to the mass of levodopa or levodopa equivalence. The concentration may be measured in units of ng/mL, to the mass of levodopa or levodopa equivalence in the formulation, where said mass is measured in mg, of between 2:1 and 6:1. The ratio may be between 2.5:1 and 5.5:1, preferably, greater than or equal to about 3:1.

The combination of immediate release components and controlled release components of the invention provide the near infusion-like profile as evident from the plateau in the LD plasma profile (see, e.g., FIG. 5). The LD Cmax itself is not clinically relevant. What is clinically relevant is the time to reach a therapeutic level of LD (e.g., an LD level of 50% Cmax) and the time maintained at or above the therapeutic level (e.g., 50% Cmax). The short time to reach a therapeutic LD level is associated with a faster "on" time for PD patients, whereas the prolonged period at or above therapeutic levels provides the desired steady "infusion-like" profile.

It is an advantage of the present invention to provide a sustained levodopa plasma concentration for a duration greater than 5 hrs and a more consistent duration with percent coefficient of variation (CV) of mean duration of levodopa plasma concentrations >50% $C_{max}$ of less than 35%, preferably less than 30%.

The skilled artisan will appreciate that daily dosages having an amount of active agent sufficient or effective to treat diseases associated with reduced or impaired dopamine levels may generally contain from about 25 mg to about 6000 mg of levodopa or levodopa equivalence dose in combination with from about 5 mg to about 1500 mg of carbidopa.

Dosage forms may contain 25-750 mg of levodopa or levodopa equivalence. Further, dosage forms may contain carbidopa ranging from 25-300 mg. For example, the controlled release oral solid formulation of the invention may comprise from about 25 mg to about 1000 mg levodopa or levodopa equivalence. Further, the controlled release oral solid formulation of the invention may comprise from about 10 mg to about 300 mg carbidopa. Further still, the controlled release oral solid formulation of the invention may comprise from about 10 mg to about 150 mg carbidopa.

By way of example, the total daily dose of levodopa from the formulations of the invention may be less than about 2500 mg. For example, the total daily levodopa dose may be between 800 mg to 2500 mg. In a further example, the total daily levodopa dose may be about 855 mg, 1140 mg, 1170 mg, 1305 mg, 1755 mg, 2205 mg, or 2340 mg. In another embodiment, the total daily carbidopa dose may be about 292.5 mg.

The dosing frequency may vary, depending on the need of the subject. For example, the dosing frequency of the formulations of the invention may be three times a day. In another example, the dosing frequency may be a maximum of five times a day.

Actual dosage levels of active ingredient in the compositions of the present invention may be varied so as to obtain an amount of active ingredient that is effective to obtain a desired therapeutic response for a particular composition. The formulations of the invention may be administered as a single dose, or may comprise of a number of smaller doses to be administered or consumed within a short period of time. It is understood that the precise dosage and duration of treatment is a function of the disease being treated and may be determined using known practices. It is to be noted that dosage values may also vary with the severity of the condition to be alleviated. It is to be further understood that for any particular subject, specific dosage regimens should be adjusted over time according to the individual need and the professional judgment of the person administering or supervising the administration of the formulations of the invention, and that the concentration ranges set forth herein are exemplary only and are not intended to limit the scope or practice of the claimed compositions.

Optimally, after administration to a patient suffering from a condition associated with reduced or impaired dopamine levels, a pharmaceutical formulation of the invention releases levodopa into the plasma of the patient at a steady or near constant level without significant decrease or fluctuation for an extended amount of time, thereby reducing motor fluctuations.

The invention also provides methods for treating a subject with Parkinson's disease or primary Parkinsonism. The method comprises administering to the subject an effective amount of any of the controlled release oral solid formulations of the invention to treat Parkinson's disease or primary Parkinsonism. In accordance with the practice of this invention, the subject may be a human.

EXAMPLES

Example 1

I. Development of LDEE-S Beads for IPX203-B12-01

Development of Core LDEE-S Beads
Preparation of Core Beads
Required amounts of LDEE-S-Dihydrate, Microcrystalline Cellulose, Fumaric acid, Povidone K29-32, ethanol and Purified Water were dispensed. The alcohol and the purified water were charged into a container and stirred using a stir bar. Povidone was slowly added into the ethanol/water mixed solvent. Mixing continued until the Povidone was completely dissolved, and the spray pump was calibrated to the target granulation spray rate.

LDEE-S-Dihydrate, Microcrystalline Cellulose, Fumaric acid, and Povidone were charged into a high shear granulator and dry mixed for 1-5 minutes at impeller speed of 75 rpm and chopper speed of 1000 rpm. The Povidone solution was sprayed into the granulation bowl and granulation continued with either ethanol or water as necessary. The granules were wet mixed for 2 minutes, after the spraying was completed.

The wet granules were extruded using the extruder (MG 55 Multi Granulator) equipped with a 0.8 mm hole size screen at extruder speed of 55 rpm. The extrudates were collected into double polyethylene lined bags. The collected extrudate was weighed and adjusted in the quantities ranging from 170-210 g per load.

One load of the weighed extrudate was charge into a spheronizer equipped with a 3 mm cross hatch disc. The extrudate was spheronized at a spheronisation speed of 1400 rpm for 1-10 mins.

The spheronized beads were discharge into double polyethylene bags. The remaining extrudate were spheronized until all the double polyethylene-lined bags are completed.

The wet beads were dried in a fluid bed drier (Glatt GPCP-1) at an Inlet temperature of 35±10° C. until Loss on Drying was not more than 5.0%. The steps above were repeated until additional sub loads had been processed.

The dried beads were passed through a mechanical sieve (Vibroscreen) equipped with a 24-MG mesh screen at the bottom, 18-MG mesh screen in the middle, and 16-MG mesh screen at the top. The beads that remained on 18-US mesh and 24-MG mesh screens were collected into double polyethylene lined bags.

Muco-Adhesive/Rate-Controlling Sub-Layer Coating

The batch yield was determined. The required amounts of Amino Methacrylate Copolymer (Eudragit® E100) and Talc were calculated and dispensed. Purified Water, Acetone and Isopropyl Alcohol were dispensed into a stainless steel container and stirred using stir bar. While stirring, Amino Methacrylate Copolymer (Eudragit® E100) was slowly added into the vortex of the mixed solvent. Mixing continued until the copolymer completely dissolved. While stirring, Talc was slowly disperse into the vortex of the solution. Mixing continued until the material was completely dispersed. The suspension was continually stirred throughout the coating process.

The spray pump was calibrated to the target coating spray rate of the peristaltic pump using the suspension solution above. The core beads were coated using Glatt GPCG 1 equipped with a Wurster insert at Inlet air temperature of 35±10° C., Atomization air pressure of 1.0-2.0 bars and Wurster partition height of 15-30 mm. During coating, the inlet air temperature, exhaust flap, and spray rate were adjusted to maintain the exhaust air temperature between 30±5° C.

After the target amount of coating solution was sprayed, the coated beads were dried at an inlet air temperature of 40±10° C. for 90 minutes. The dried beads were passed through a mechanical sieve (Vibroscreen) equipped with a pan at the bottom, 14-MG mesh screen in the middle, and 12-MG mesh screen at the top. The beads that remained in the pan and 14-MG mesh screens were collected into double polyethylene lined bags.

Enteric Coating

The batch yield was determined. Based on the batch yield, the required amounts of Triethyl Citrate, Talc and an enteric copolymer, either Methacrylic Acid Copolymer, Type A, (Eudragit® L100)/Methacrylic Acid Copolymer, Type B, (Eudragit® S) at ½ weight ratio for IPX203-C0006 or Eudragit® L100-55 for IPX203-C0004 and IPX203-C0005 were calculated and dispensed. Acetone and Isopropyl Alcohol for IPX203-C0006 or Acetone, Isopropyl Alcohol and purified water for IPX203-C0004 and IPX203-C0005 were dispensed into a stainless steel container and stirred using stir bar. While stirring, the enteric copolymer and Triethyl Citrate were added slowly into the vortex of the mixed solvent. Mixing continued until the copolymer was completely dissolved.

While stirring, Talc was added slowly into the vortex of the solution. Mixing continued until the material was completely dispersed. The suspension was continually stirred throughout the coating process. The spray pump was calibrated to the target coating spray rate of the peristaltic pump using the suspension solution.

Eudragit® E-coated beads were coated with the enteric composition using Glatt GPCG 1 equipped with a Wurster insert at Inlet air temperature of 35±10° C., Atomization air pressure of 1.0-2.0 bars and Wurster partition height of 15-30 mm. During coating, the inlet air temperature, exhaust flap, and spray rate were adjusted to maintain the exhaust air temperature between 30±5° C.

After the target amount of coating solution was sprayed, the enteric-coated beads were dried at an inlet air temperature of 40±10° C. for 120 minutes. The dried beads were passed through a mechanical sieve (Vibroscreen) equipped with a pan at the bottom, 14-MG mesh screen in the middle, and 12-MG mesh screen at the top. The beads that remained in the pan and 14-MG mesh screens were collected into double polyethylene lined bags.

Encapsulation

The batch yield was determined. Based on the batch yield, the required amounts of the enteric coated beads (also referred to herein as beads having an outer enteric coating polymer layer) and talc were calculated and dispensed. The Enteric Coated Beads and Talc were placed in an appropriated sized plastic bag and were manually blended by shaking the plastic bag with the beads and Talc for 10 minutes. The blend was encapsulated with 00 size gelatin capsules, using MG Flexalab Encapsulator at the target fill weight of 482 mg, 537 mg and 472 mg for IPX203-C0004, IPX203-C0005 and IPX203-C0006 respectively, so that the target LDEE dose/2 capsules was 228 mg, equivalent to LD dose of 200 mg.

Rationale for Components and Coatings in Formulation

The core bead formulation was developed utilizing microcrystalline cellulose (MCC) as filler since the wetted MCC has the desired rheological properties, cohesiveness, and plasticity to yield strong beads. An MCC level at 30% was selected and it was found to provide beads with acceptable sphericity and support a robust manufacturing process. Because LDEE-S is more stable in acidic environment, in order to reduce the LDEE degradation inside the beads during the long release duration, a 5% fumaric acid is added in the formulation to lower the microenvironment pH. An extra binder povidone at 1% level is also added to the formulation with the intent to provide a more robust extrusion process. The dissolution profile of the core beads is fast, with the complete release within 30 min, as measured in a USP Apparatus 1 with basket speed of 75 rpm in pH 7 phosphate buffer.

To control the release of LDEE-S, the core LDEE-S beads are coated with different release polymers. Eudragit® E100 is swellable and permeable above pH 5. It is used as an inner coating to slowly release drug at intestinal pH. As such, the use of Eudragit® E100 coating results in a controlled release of LDEE-S. Furthermore, to protect the Eudragit® E layer as well as to direct the release of LDEE-S to the more alkaline region (i.e., intestinal region and not the stomach region), an enteric coating is applied as an outer coat.

Development of Eudragit® E100 Coated LDEE-S Beads

Prototype formulations with different Eudragit® E100 coating content were developed and evaluated based on the in vitro dissolution profiles in pH 7 phosphate buffer solution. Analysis of the effect of coating thickness on LDEE release indicates that increasing the coating level decreases the in vitro release of active pharmaceutical ingredient (API) and although polymer has the sustained-release effect, its permeability is relatively large, thus a thick coating is required to prepare formulations with longer release duration (T90>5 hr).

In the final polymer coating formulation, talc was also added as a lubricant to facilitate the fluid bed coating process at a ratio of Eudragit® E100/talc at 10/1.

Development of Enteric Coating of Eudragit® E100 Coated LDEE-S Beads

Initially, the enteric coating chosen at the development stage was Eudragit® S100 and L100 at a ratio of 2:1, and the ratio among polymer and other components was Eudragit® polymer:triethyl citrate (TEC):Talc ratio of 7:2:1.

The in vitro dissolution profiles of prototype enteric coated beads (already coated with Eudragit® E100 at a coating level of 65% w/w) coated with different levels of enteric film. The results showed that a coating level of 23% provides an adequate acid protection with less than 5% LDEE released in acidic medium. Further, with less enteric coating level (≤10%), there is ~20% LDEE released in acidic medium, and no significant difference in drug release profiles when coated at 5% or 10%.

When the dissolution was done in pH 1 solution for 2 hr and then switch to pH 7 buffer, even with outer enteric coating layer, the permeability of inner Eudragit® E100 layer may increase after 2 hr in pH 1.0 medium, since T90 was around 6.5 hr in pH 7 buffer for Eudragit® E coated beads but shortened to ~4.5 hr in pH 7 buffer for enteric coated beads after switch over of dissolution medium.

For IPX203-B12-01, enteric polymer coatings that can dissolve at lower pH were also developed, in which Eudragit® L100-55 (dissolve above pH 5.5) was used instead of Eudragit® S100 and L100. The ratio among polymer and other components in the coating formulation was Eudragit® L100-55:TEC:Talc of 6:1:3.

Dissolution Medium pH Effect on LDEE Release from Enteric Coated Beads

The effect of pH on the release of LDEE from the LDEE-S core beads coated with Eudragit® E (65% w/w) and enteric coat (Eudragit® S100/L100 at 2/1) was conducted at pH 1.0 solution for 2 hr and then switch to pH 6.6, 6.8, 7.0 buffer solutions.

The results indicated that with less enteric layer coated (10%) or thinner enteric outer coating, drug release was earlier, and conversely, with a thicker enteric outer coating (23%), drug release was delayed at all pH's compared to the thinner enteric outer coated LDEE-S core beads. Further, with less or thinner enteric outer coating, there was no effect on drug release when pH changed from 6.6 to 6.8, and the drug release was slower when pH changed to 7.0. However, when thicker enteric coat layer was applied (23%), there was no effect on drug release when pH changed from 6.8 to 7.0, but the drug release was much slower when pH changed to 6.6. Additionally, the pH value in dissolution medium can affect drug release profiles through its effect on both enteric coating layer dissolution and Eudragit® E layer permeability. When enteric coat layer is thin, its dissolution is fast and the pH effect on Eudragit® E is more a rate-limiting factor. Since Eudragit® E permeability decreases with increasing pH, slower release was observed in pH 7.0 medium. However, with a thicker enteric coat, the dissolution of the enteric layer is much slower and become a rate-limiting step. With a combination of Eudragit® S100 and L100 at a ratio of 2/1, its dissolution at lower pH (pH 6.6) is much slower than at pH above 6.8. Thus the drug release is much slower in pH 6.6 medium with a thicker enteric coating.

Final Formulation of LDEE-S Beads for IPX203-B12-01

The test formulations for IPX203-B12-01 are summarized in Table 1. The composition of the formulations of LDEE-S beads (IPX203-C0004, IPX203-C0005 and IPX203-C0006) is summarized in Table 2. FIG. 2 shows the in vitro dissolution profiles of those formulations. IPX203-C0006 was coated with 10% (w/w) enteric coat (Eudragit® S100/L100 at 2/1), which released ~20% drug in the first 2 hr in pH 1.0 solution. After dissolution medium switch to pH 7 buffer, drug was controlled released over a period T90~3 hr. A better acidic protection for IPX203-0004 and IPX203-C0005 was observed due to their thicker enteric coat layer (25% w/w, Eudragit® L100-55). Formulations IPX203-C0004 has a thinner Eudragit® E100 layer of coating compared to IPX203-C0005, and has T90~3 hr in pH 7 buffer. IPX203-C0005 provided longer release duration (T90~5 hr in pH 7 buffer).

TABLE 1

Test Formulations of IPX203 Prototype Capsule in Single Dose Relative Bioavailability (BA) Studies IPX203-B12-01*.

| Test Formulation | Study | LDEE (mg/2 capsules) |
| --- | --- | --- |
| IPX203-C0004 | IPX203-B12-01 | 228 |
| IPX203-C0005 | | 228 |
| IPX203-C0006 | | 228 |

*Carbidopa was dosed as commercial product Lodosyn ® 25 mg/tablet with the dosing regimen: 25 mg at T = 0 and 6.25 mg (¼ tablet) at T = 4 hr.

TABLE 2

Composition of Final Formulation of LDEE-S Beads for IPX203-B12-01

| | Composition (w/w %) | | |
| --- | --- | --- | --- |
| Ingredient | IPX203-C0004 | IPX203-C0005 | IPX203-C0006 |
| Levodopa Ethyl Ester Succinate, Dihydrate | 31.76 | 28.50 | 32.39 |
| Microcrystalline Cellulose, NF | 14.66 | 13.15 | 14.95 |
| Fumaric Acid, NF | 2.44 | 2.19 | 2.49 |
| Povidone, USP (Plasdone K-29/32) | 0.49 | 0.44 | 0.50 |
| Amino Methacrylate Copolymer, NF (Eudragit ® E100) | 27.14 | 31.74 | 36.08 |
| Methacrylic Acid Copolymer, Type C, NF (Eudragit ® L100-55) | 11.88 | 11.88 | — |
| Methacrylic Acid Copolymer, Type A, NF (Eudragit ® L 100) | — | — | 2.10 |
| Methacrylic Acid Copolymer, Type B, NF (Eudragit ® S 100) | — | — | 4.20 |
| Triethyl Citrate, NF | 1.98 | 1.98 | 1.80 |
| Talc, USP | 9.64 | 10.12 | 5.50 |
| Total | 100.0 | 100.0 | 100.0 |

II. In Vivo Results of IPX203-B12-01

The in vivo performance of the prepared formulations IPX203-C0004, IPX203-C0005 and IPX203-C0006 has been evaluated in healthy volunteers in a relative bioavailability analysis of IPX203-B12-01. The study design was a randomized, single-dose, crossover study in 15 normal, healthy volunteers under fasting condition.

FIG. 3 shows the plasma profile for the multi-particulate formulations IPX203-C0004, IPX203-C0005 and IPX203-C0006 in comparison with Sinemet® CR. All the IPX 203 multi-particulate formulations comprise Eudragit® E coating. The relative bioavailability parameters are provided in Table 3. Comparison of the LD plasma concentration profile of the tested formulations to the reference product Sinemet® CR indicate that both IPX203-C0005 and IPX203-C0006 showed sufficient AUC but more extended effect than Sinemet® CR. Further, the difference of Tmax between IPX203-C0004 and IPX203-C0005 corresponds well with their difference in in vitro dissolution profiles. Also, although the in vitro release profiles for IPX203-C0004 and IPX203-C0006 showed similar T90 (~3 hr) after switch to pH 7 buffer, IPX203-C0006 showed more delayed effect in vivo. Additionally, the results show that IPX203-C0006 has Cmax and AUC comparable to those of Sinemet® CR.

TABLE 3

Relative LD Bioavailability Parameters of IPX203 Capsules Tested in Bioavailability Analysis of IPX203-B12-01 (n = 15).

| Test Formulation | CD-LDEE (mg)[a] | | % Ratio of Test/ Sinemet® CR | | Duration LD Concentration >50% |
|---|---|---|---|---|---|
| | LDEE | CD | $AUC_{0-\infty 0-}$ | $C_{max}$ | Cmax (h)[b] |
| IPX203-C0004 | 228 | 31.25 | 80 | 86 | 2.9 (3.3) |
| IPX203-C0005 | 228 | | 97 | 97 | 3.15 (3.25) |
| IPX203-C0006 | 228 | | 87 | 104 | 3.25 (3.25) |

[a]LDEE 228 mg is equivalent to LD 200 mg.
[b]Sinemet® CR tablet $t_{max}$ = 2.5 hr Example 2

I. Processing Procedures for Levodopa Ethyl Ester Succinate (LDEE-S)/Carbidopa (CD) Capsules for IPX203 B13-01

Preparation of Core Beads for IPX203-C0012, IPX203-C0013 and IPX203-C0016

Required amounts of LDEE-S-Dihydrate, Microcrystalline Cellulose, Fumaric acid, Povidone K29-32, ethanol and Purified Water were dispensed. The alcohol and the purified water were charged into a container and stirred using stir bar, Povidone was slowly added into the ethanol/water mixed solvent. Mixing continued until the Povidone was completely dissolved, and the spray pump was calibrated to the target granulation spray rate.

LDEE-S-Dihydrate, Microcrystalline Cellulose, Fumaric acid, and Povidone were charged into a high shear granulator and dry mixed for 1-5 minutes at impeller speed of 75 rpm and chopper speed of 1000 rpm. The Povidone solution was sprayed into the granulation bowl and granulation continued with either ethanol or water as necessary. The granules were wet mixed for 2 minutes, after the spraying was completed.

The wet granules were extruded using the extruder (MG 55 Multi Granulator) equipped with a 0.8 mm hole size screen at extruder speed of 55 rpm. The extrudates were collected into double polyethylene-lined bags. The collected extrudate was weighed and adjusted in the quantities ranging from 180-240 g per load.

One load of the weighed extrudate was charge into a spheronizer equipped with a 3 mm cross hatch disc. The extrudate was spheronized at a spheronisation speed of 1400 rpm for 1-10 mins. The spheronized beads were discharge into double PE bags. The remaining extrudate were spheronized until all the double polyethylene-lined bags are completed.

The wet beads were dried in a fluid bed drier (Glatt GPCP-1) at an Inlet temperature of 35±10° C. until Loss on Drying is not more than 5.0%. The steps above were repeated until additional sub loads have been processed.

The dried beads were passed through a mechanical sieve (Vibroscreen) equipped with a 24-MG mesh screen at the bottom, 18-MG mesh screen in the middle, and 16-MG mesh screen at the top. The beads that remained on 18-US mesh and 24-MG mesh screens were collected into double polyethylene-lined bags.

Rate-Controlling Membrane Coating for IPX203-C0012 and IPX203-C0013
IPX203-C0012 Beads Batch yield was determined. Based on the batch yield, the required amounts of Cellulose Acetate (CA) and Polyethylene Glycol 3350 (PEG3350) at weight ratio (CA/PEG) of 95/5 and Acetone/Purified Water (95/5 w/w) were calculated and dispensed. The Acetone was dispensed into a stainless steel container and stirred using stir bar. While stirring, Cellulose Acetate (CA) was added slowly into the vortex of the solvent and mixing was continued until the copolymer completely dissolved.

The Purified Water was dispensed into another stainless steel container and was stirred using a stir bar. While stirring, Polyethylene Glycol 3350 (PEG3350) was added slowly into the vortex of the purified water solvent and mixing was continued until the copolymer completely dissolved. While stirring, PEG solution was added quickly into the CA solution and mixing was continued until the solution was clear. Spray pump was calibrated to the target coating spray rate of the peristaltic pump using the clear solution and the core beads were coated using Glatt GPCG 1 equipped with a Wurster insert at Inlet air temperature of 33±10° C., Atomization air pressure of 1.0-2.0 bars and Wurster partition height of 20-40 mm. During coating, the inlet air temperature, exhaust flap, and spray rate were adjusted to maintain the exhaust air temperature between 30±5° C.

After the target amount of coating solution was sprayed, the coated beads were dried at an inlet air temperature of 35±10° C. for 40-60 minutes. The dried beads were passed through a mechanical sieve (Vibroscreen) equipped with a pan at the bottom and a 14-MG mesh screen at the top, and collected the beads that passed through the 14-MG mesh screen were collected in double polyethylene-lined bags. Oversized beads that remained on the 14-MG mesh screen were rejected.

IPX203-C0013 Beads

The procedure for preparing the coating solution and the coating conditions are identical to those for IPX203-C0012 coating. However, the rate-controlling polymer is Cellulose Acetate (CA), and the solvent is Acetone.

Muco-Adhesive Coating for IPX203-C0012, IPX203-C0013 and IPX203-C0016

The batch yield was determined. The required amounts of Amino Methacrylate Copolymer (Eudragit® E100) and Talc were calculated and dispensed at weight ratio of 91/9. Purified Water, Acetone and Isopropyl Alcohol were dispensed at weight ratio of 12/68/20 into a stainless steel container and stirred using stir bar. While stirring, Amino Methacrylate Copolymer (Eudragit® E100) was slowly added into the vortex of the mixed solvent. Mixing continued until the copolymer completely dissolved. While stirring, Talc was slowly dispersed into the vortex of the solution. Mixing continued until the material was completely dispersed. The suspension was continually stirred throughout the coating process.

The spray pump was calibrated to the target coating spray rate of the peristaltic pump using the suspension solution above. The rate-controlling membrane-coated beads for IPX203-C0012 and IPX203-C0013, or the core beads for IPX203-C0016 were coated with the muco-adhesive coating composition Glatt GPCG 1 equipped with a Wurster insert at Inlet air temperature of 35±10° C., Atomization air pressure of 1.0-2.0 bars and Wurster partition height of 15-40 mm.

During coating, the inlet air temperature, exhaust flap, and spray rate were adjusted to maintain the exhaust air temperature between 30±10° C.

After the target amount of coating solution was sprayed, the coated beads were dried at an inlet air temperature of 40±10° C. for 60-120 minutes. The dried beads were passed through a mechanical sieve (Vibroscreen) equipped with a pan at the bottom and a 14-MG mesh screen at the top. The beads that passed through 14-MG mesh screen were collected into double polyethylene-lined bags and the oversized beads that remained on the 14-MG mesh screen were rejected.

Enteric Coating for IPX203-C0012, IPX203-C0013 and IPX203-C0016

The batch yield was determined. Based on the batch yield, the required amounts of Triethyl Citrate, Talc and an enteric copolymer, either Methacrylic Acid Copolymer, Type A, (Eudragit® L100)/Methacrylic Acid Copolymer, Type B, (Eudragit® S) at ½ weight ratio for IPX203-C0012 and IPX203-C0016 or Eudragit® L100 for IPX203-C00013 were calculated and dispensed. Acetone and Isopropyl Alcohol were dispensed at weight ratio of 40/60 into a stainless steel container and stirred using stir bar. While stirring, the enteric copolymer and Triethyl Citrate (TEC) were added slowly into the vortex of the mixed solvent and mixing was continued until the enteric copolymer completely dissolved. While stirring, Talc was slowly dispensed into the vortex of the solution and mixing was continued until the material was completely dispersed. The suspension was continuously stirred throughout the coating process. The weight ratio of enteric copolymer/TEC/Talc was 70/20/10.

The spray pump was calibrated to the target coating spray rate of the peristaltic pump using the solution, and the Eudragit® E-coated beads were coated using Glatt GPCG 1 equipped with a Wurster insert at Inlet air temperature of 35±10° C., Atomization air pressure of 1.0-2.0 bars and Wurster partition height of 15-30 mm. During coating, the inlet air temperature, exhaust flap, and spray rate were adjusted to maintain the exhaust air temperature between 30±5° C. After the target amount of coating solution was sprayed, the coated beads were dried at an inlet air temperature of 40±10° C. for 60-120 minutes and the dried beads were passed through a mechanical sieve (Vibroscreen) equipped with a pan at the bottom and a 14-MG mesh screen at the top. The beads that passed through 14-MG mesh screen were collected into double polyethylene-lined bags, and oversized beads that remained on the 14-MG mesh screen were rejected.

Immediate Release Granules (CD/LDEE-S)

The required amount of 27% Carbidopa USP, 49.9% Levodopa Ethyl Ester Succinate-Dihydrate, 12.2% Dibasic Calcium Phosphate Anhydrous, 7.0% Hydroxypropyl Cellulose (Klucel-EXF), and 2.0% Croscarmellose Sodium, (Ac-Di-Sol) were dispensed and charged into the granulation bowl of a high shear granulator. The components were dry-mixed for 1-3 mins at impeller speed between 150-250 rpm and Chopper Speed of 1000 rpm. Purified Water was sprayed at a desired flow rate into the granulation bowl until consistent wet mass was reached. The water/dry blend weight ratio was between 0.20-0.40. The granules were wet-mixed for additional 1-5 minutes, after the spraying was completed. The wet granules were charged into the top spray product bowl of GPCG 1 and dried using GPCG 1 at inlet air temperature of 50° C. until the LOD is less than 6.0%. Inlet air flow was adjusted to maintain the fluidization of the wet granules. The dried granules from the bowl were transferred into clean, double polyethylene-lined containers, and the granules were passed through the Fitzmill equipped with a stainless steel #24 mesh screen at Knife Mode and speed of 2000-3000 rpm. The required amount of Talc was calculated based on the weight of the milled granules and 2% Talc of the immediate release granules. The milled granules and Talc were charged into Pharmatech Miniblender and blended for 5 minutes. The blend was discharged into clean, double polyethylene-lined containers.

Encapsulation

The batch yield was determined. Based on the batch yield, the required amounts of the Enteric Coated Beads and Talc (at weight ratio of 99/1) were calculated and dispensed. The Enteric Coated Beads and Talc were charged into an appropriated sized plastic bag and manually blended by shaking the plastic bag for 10 minutes. The blend and Immediate Release Granules (CD/LDEE-S) were encapsulated with 00 size gelatin capsules, using MG Flexalab Encapsulator. For IPX203-C0016, the blend was encapsulated but the Immediate Release Granules (CD/LDEE-S) were not. Table 4 shows the target fill weight for IPX203-C0012, IPX203-C0013 and IPX203-C0016 and Table 5 lists the composition of IPX203-C0012, IPX203-C0013 and IPX203-C0016.

TABLE 4

Target Fill Weight of IPX203-C0012, IPX203-C0013 and IPX203-C0016

| | Target Fill Weight (mg/Capsule) | |
|---|---|---|
| | Enteric-coated Beads | Immediate release Granules |
| IPX203-C0012 | 389.5 | 200.0 |
| IPX203-C0013 | 412.0 | 200.0 |
| IPX203-C0016 | 252.6 | N/A |

TABLE 5

Formulation Composition of IPX203-C0012, IPX203-C0013 and IPX203-C0016

| Ingredient | IPX203-C0012 Amount (mg/capsule) | IPX203-C0012 % (w/w) | IPX203-C0013 Amount (mg/capsule) | IPX203-C0013 % (w/w) | IPX203-C0016 Amount (mg/capsule) | IPX203-C0016 % (w/w) |
|---|---|---|---|---|---|---|
| Carbidopa, USP | 54.0 | 9.2 | 54.0 | 8.8 | | |
| Levodopa Ethyl Ester Succinate, Dihydrate | 306.4 | 52.0 | 306.4 | 50.1 | 81.8 | 32.4 |
| Microcrystalline Cellulose, NF | 95.4 | 16.2 | 95.4 | 15.6 | 37.7 | 14.9 |
| Amino Methacrylate Copolymer, NF (Eudragit® E100) | 33.1 | 5.6 | 33.4 | 5.5 | 91.1 | 36.1 |
| Fumaric Acid, NF (Fine Granules) | 15.9 | 2.7 | 15.9 | 2.6 | 6.3 | 2.5 |
| Cellulose Acetate, NF (CA-398-10 NF) | 9.1 | 1.5 | 12.9 | 2.1 | 0.0 | |
| Talc, USP | 13.1 | 2.2 | 15.2 | 2.5 | 13.9 | 5.5 |
| Methacrylic Acid Copolymer, Type B, NF (Eudragit® S100) | 8.5 | 1.4 | | | 10.6 | 4.2 |
| Methacrylic Acid Copolymer, Type A, NF (Eudragit® L100) | 4.3 | 0.7 | 25.9 | 4.2 | 5.3 | 2.1 |
| Triethyl Citrate, NF | 3.7 | 0.6 | 7.4 | 1.2 | 4.5 | 1.8 |
| Povidone, USP (Plasdone, K-29/32) | 3.2 | 0.5 | 3.2 | 0.5 | 1.3 | 0.5 |
| Polyethylene Glycol, NF | 0.5 | 0.1 | | | | |
| Dibasic Calcium Phosphate, Anhydrous | 24.3 | 4.1 | 24.3 | 4.0 | | |
| Hydroxypropyl Cellulose, NF (Klucel-EXF) | 14.0 | 2.4 | 14.0 | 2.3 | | |
| Croscarmellose Sodium, NF (Ac-Di-Sol) | 4.0 | 0.7 | 4.0 | 0.7 | | |
| Total | 589.5 | 100.0 | 612.0 | 100.0 | 252.6 | 100.0 |

*54 mg of Carbidopa, USP is equivalent to 50 mg of Carbidopa anhydrate.
**306 mg of Levodopa Ethyl Ester Succinate-Dihydrate is equivalent to 228 mg of Levodopa Ethyl Ester and to 200 mg Levodopa.

II. Processing Procedures for Manufacturing Entacapone Capsules for IPX203 B13-01

Preparation of Core Beads for IPX203-C0014 Capsule

The required amount of Entacapone, Microcrystalline Cellulose, Povidone K29-32 and Purified Water were dispensed. The purified water was charged into a container and stirred using a stir bar, the Povidone (1.0% of the solid blend) slowly added into the water at Povidone/Water weight ratio of 6/133.2 and mixing continued until the Povidone was completely dissolved. The spray pump was calibrated to the target granulation spray rate (23 g/min), and 84.0% Entacapone and 15.0% Microcrystalline Cellulose were charged into a high shear granulator and were dry mixed for 1-5 minutes at impeller speed of 200-300 rpm and chopper speed of 1400-1600 rpm. The solution was sprayed into the granulation bowl until all the solution was sprayed, and granulation was continued with Purified Water as necessary. The granules were wet-mixed for 2 minutes, after the spraying was completed. Then the wet granules were extruded using the extruder (MG 55 Multi Granulator) equipped with a 0.8 mm hole size screen at extruder speed of 50 rpm. The extrudates were collected into double polyethylene-lined bags. Further, the collected extrudate were weighed and adjusted in the quantities ranging from 200-210 g per load.

One load of the weighed extrudate was charged into a spheronizer equipped with a 3 mm cross hatch disc and spheronized at spheronisation speed of 1000 rpm for 1-2 mins. The spheronized beads were discharged into double PE bags. The wet beads were dried in a fluid bed drier (Glatt GPCP-1) at an Inlet temperature of 35±10° C. until Loss on Drying was not more than 5.0%. The dried beads were passed through a mechanical sieve (Vibroscreen) equipped with a pan at the bottom, 24-MG mesh screen in the middle, and 16-MG mesh screen at the top. The beads that were retained on 24-MG mesh were collected into double polyethylene-lined bags, and the beads on the pan and 16-MG mesh screen were rejected.

Enteric Coating for IPX203-C0014

The required amounts of Triethyl Citrate, Talc, Methacrylic Acid Copolymer Dispersion, NF (Eudragit® L30D-55) and Water were calculated and dispensed. The Purified Water was dispensed into a stainless steel container and stirred using a stir bar. While stirring, Triethyl Citrate (TEC), Talc and the enteric copolymer dispersion were slowly added into the vortex of Purified Water, and mixing was continued until the material was completely dispersed. The suspension was stirred throughout the coating process. The weight ratio of enteric copolymer/Talc/TEC was 63.0/30.7/6.3.

The spray pump was calibrated to the target coating spray rate of the peristaltic pump using the solution, and the core beads were coated using Glatt GPCG 1 equipped with a Wurster insert at Inlet air temperature of 35±10° C., Atomization air pressure of 1.0-2.0 bars and Wurster partition height of 15-30 mm. During coating, the inlet air temperature, exhaust flap, and spray rate were adjusted to maintain the exhaust air temperature between 30±5° C.

After the target amount of coating solution was sprayed, the coated beads were dried at an inlet air temperature of 30±10° C. until the moisture level was below 5%. The dried beads were passed through a mechanical sieve (Vibroscreen) equipped with a pan at the bottom and a 12-MG mesh screen at the top. The beads that passed through the 12-MG mesh screen were collected into double polyethylene-lined bags, and the oversized beads that remained on the 12-MG mesh screen were rejected.

Encapsulation for IPX203-C0014

The required amounts of the Enteric Coated Beads and Talc (at weight ratio of 99/1) were calculated and dispensed, and the Enteric Coated Beads and Talc were charged into an appropriate sized plastic bag. The beads and Talc were manually blended by shaking the plastic bag for at least 5 minutes. The blend was encapsulated with 00 size gelatin capsules, using MG Flexalab Encapsulator. The target fill weight was 505 mg. Table 6 lists the composition of IPX203-C0014.

TABLE 6

Formulation Composition of Entacapone Capsule (IPX203-C0014)

| Ingredient | % (w/w) | Amount (mg/capsule) |
|---|---|---|
| Entacapone | 79.2 | 400.0 |
| Microcrystalline Cellulose, NF (Avicel PH-101) | 14.1 | 71.4 |
| Povidone, USP (Plasdone, K-29/32) | 1.0 | 4.8 |
| Methacrylic Acid Copolymer Dispersion, NF (Eudragit® L30D-55) | 3.0 | 15.0 |
| Talc, USP | 2.4 | 12.3 |
| Triethyl Citrate, NF | 0.3 | 1.5 |
| Total | 100.0 | 505.0 |

III. In Vitro Release Profiles of Final LDEE-S-Dihydrate Dosage Forms for Pharmacokinetic (IPX203-B13-01)

Table 7 lists the test regimen for the 5-arm cross-over PK analysis (IPX203 B13-01).

TABLE 7

Dosing Regimen for IPX203 B13-01

| Regimen | Dosage Form | CD/capsule | LD/capsule | Entacapone/capsule |
|---|---|---|---|---|
| Regimen A | IPX203-C0012 | 50 mg | 200 mg* | N/A |
| Regimen B | IPX203-C0012 + IPX203-C0014 | 50 mg | 200 mg* | 400 mg |
| Regimen C | IPX203-C0013 + IPX203-C0014 | 50 mg | 200 mg* | 400 mg |
| Regimen D | IPX203-C0013 + IPX203-C0016 + IPX203-C0014 | 50 mg | 255.6 mg* | 400 mg |
| Regimen E | Stalevo® 150 mg | 37.5 mg | 150 mg | 200 mg |

*LD equivalent dose based on total amount of LDEE-S-Dihydrate in the formulation The in vitro release profiles of the regimen A-D were measured using USP I dissolution method at agitation speed of 75 rpm in Simulated Gastric Fluid (pH 1.0) for first 2 hrs and followed by in Simulated Intestinal Fluid (pH 7.0). FIG. 4 shows the release profiles of these test regimens. The T90 (time duration for 90% of LDEE-S-Dihydrate released) is approximately 3 hr, 4.5 h and 6 hrs for Regimen B, C and D, respectively. The LDEE-S-Dihydrate capsule (C0012) was used in both Regimen A and Regimen B.

IV. In Vivo Evaluation (IPX203-B13-01)

The in vivo performance of the prepared dosage forms IPX203-C00012, IPX203-C00013 and IPX203-C00014 and IPX203-C0016 has been evaluated in 12 healthy volunteers under fasted condition in a relative bioavailability analysis of IPX203-B13-01. The four test treatments were:

Regimen A: C0012

Regimen B: C0012+C0014

Regimen C: C0013+C0014

Regimen D: C0013+C0016+C0014

Regimen E: Stalevo 150 (Reference)

Where

C0012 contained 228 mg LDEE ER beads with T90~3 hrs and 50 mg CD

C0013 contained 228 mg LDEE ER beads with T90~5 hrs and 50 mg CD

C0014 contained 400 mg enteric-coated entacapone

C0016 contained 77 mg LDEE ER beads with T90~12 hrs

FIG. 5 shows the levodopa plasma profiles for all these regimens. Based on the in vivo plasma profiles depicted in FIG. 5, the in vivo plasma profiles correlates well with the in vitro dissolution profiles depicted in FIG. 4. FIG. 5 demonstrates that Regimen D has the longest therapeutic coverage and a constant plasma profile.

Example 3

Prepared Carbidopa Beads

The core beads of CD beads were formulated based on the granulation-extrusion-spheronisation technology. 30 w/w % MCC was used in the core seed formulation. No controlled release coating layer was needed. CD core beads was enteric-coated with the enteric coating formulation comprising EUDRAGIT® S100 and L100 at a ratio of 2:1. The enteric coating level was 5%. Table 8 summarized the composition of final formulation of CD beads.

TABLE 8

Composition of Formulation of CD Beads

| Ingredient | Composition (w/w %) |
|---|---|
| Carbidopa | 66.44 |
| Microcrystalline Cellulose, NF | 28.47 |
| Methacrylic Acid Copolymer, Type A, NF (Eudragit® L 100) | 1.14 |
| Methacrylic Acid Copolymer, Type B, NF (Eudragit® S 100) | 2.35 |
| Triethyl Citrate, NF | 1.00 |
| Talc, USP | 0.60 |
| Total | 100.0 |

Example 4

The preparation procedure in Example 1 was repeated in this example, except the coating compositions. The core beads were coated first with either cellulose acetate polymer or a combination of Hypromellose and ethylcellulose. The coated beads were further coated with chitosan or polycarbophil or Eudragit® E100. After the second layer coating, the beads were further coated with Eudragit® L100-55. Table 9 shows the composition of four formulations IPX203-C0007, IPX203-C0008, IPX203-C0009 and IPX203-C0010.

TABLE 9

Composition of Formulations of LDEE-S Beads Using Chitosan or Polycarbophil as Muco-adhesive Polymers

| Ingredient | IPX203-C0007 | IPX203-C0008 | IPX203-C0009 | IPX203-C0010 |
|---|---|---|---|---|
| Levodopa Ethyl Ester Succinate, Dihydrate | 39.45 | 45.18 | 31.14 | 45.30 |
| Microcrystalline Cellulose, NF | 18.21 | 20.85 | 14.37 | 20.91 |
| Fumaric Acid, NF | 3.03 | 3.48 | 2.40 | 3.48 |
| Povidone, USP (Plasdone, K-29/32) | 0.61 | 0.70 | 0.48 | 0.70 |
| Hypromellose, Type 2910, USP (Pharmacoat 606, 6 cps) | 2.82 | — | 2.23 | 4.22 |
| Ethylcellulose, NF (Ethocel, Standard-10 FP Premium) | 11.28 | — | 8.90 | 16.89 |
| Polycarbophil, USP (Noveon ® AA-1) | 3.77 | — | — | 4.57 |
| Cellulose Acetate, NF (CA-398-10 NF) | — | 4.21 | — | — |
| Chitosan, NF (ChitoPharm ® S) (Material #50222178) | — | 3.74 | — | — |
| Glacial Acetic Acid, USP | — | 1.01 | — | — |
| Amino Methacrylate Copolymer, NF (Eudragit ® E100) | — | — | 17.86 | — |
| Methacrylic Acid Copolymer, Type C, NF (Eudragit ® L100-55) | 11.91 | 11.91 | 11.90 | 1.76 |
| Triethyl Citrate, NF (PG) | 1.99 | 1.99 | 1.98 | 0.29 |
| Talc, USP | 6.94 | 6.93 | 8.73 | 1.87 |
| Total | 100.0 | 100.0 | 100.0 | 100.0 |

Example 5

I. Formulations for IPX203-B14-01 Biostudy

Four test formulations were evaluated in biostudy IPX203-B14-01. For IPX203-C0023, -C0024, and -C0025 formulations, there were two components in one capsule. For IPX203-C0026, there were three components in one capsule. Table 10 below showed the formulation information for each product, and Tables 11-13 showed formulation composition for each component.

TABLE 10

Test Formulations for Relative Bioavailability Study IPX203-B14-01

| Test Formulation | Component I: IR CD (mg) | Component I: IR LD (mg) | Component II: LD ER Prototype/LD (mg) | Entacapone (ENT) Component ENT (mg) |
|---|---|---|---|---|
| IPX203-C0023 | 50 | 80 | Prototype I/280 | 0 |
| IPX203-C0024 | | | Prototype III/280 | |
| IPX203-C0025 | | | Prototype II/280 | |
| IPX203-C0026 | | | Prototype II/280 | 200 |
| Stalevo ® 100 (Reference) | | | CD/LD/ENT (25/100/200 mg) | |

TABLE 11

Composition of Prototype Formulations of IPX203 Component II

| Ingredient | Prototype I | Prototype II | Prototype III |
|---|---|---|---|
| Core bead | | | |
| levodopa | 65.26 | 62.15 | 61.03 |
| Microcrystalline Cellulose | 8.82 | 8.40 | 8.25 |
| Mannitol | 8.82 | 8.40 | 8.25 |
| Sodium Lauryl Sulfate | 4.41 | 4.20 | 4.12 |
| Povidone | 0.88 | 0.84 | 0.82 |
| CA/Copovidone layer (1st layer) | | | |
| Cellulose Acetate | — | 1.89 | 1.85 |
| Copovidone | — | 2.31 | 2.27 |
| Eudragit ® E100 layer (2nd layer) | | | |
| Eudragit ® E100 | 6.42 | 6.41 | 3.93 |
| Talc | 0.63 | 0.65 | 0.40 |
| Enteric layer (3rd layer) | | | |
| Eudragit ® L100 | 3.34 | 3.33 | 6.36 |
| Triethyl Citrate | 0.96 | 0.95 | 1.81 |
| Talc | 0.47 | 0.48 | 0.91 |
| Total | 100.0 | 100.0 | 100.0 |

TABLE 12

Composition for Component I Formulation

| Ingredient | Composition (w/w %) |
|---|---|
| Carbidopa | 35.86 |
| Levodopa | 53.14 |
| Croscarmellose Sodium | 7.00 |
| Povidone | 3.00 |
| Magnesium Stearate | 1.00 |
| Total | 100.0 |

TABLE 13

Formulation Composition for Entacapone Component

| Ingredient | % (w/w) |
|---|---|
| Entacapone | 73.15 |
| Microcrystalline Cellulose, NF (Avicel PH-101) | 14.25 |
| Povidone, USP (Plasdone, K-29/32) | 1.90 |
| Sodium Starch Glycolate | 3.80 |
| Sodium Lauryl Sulfate, NF | 1.90 |
| Methacrylic Acid Copolymer, Type A, NF (Eudragit ® L100) | 3.50 |
| Talc, USP | 0.50 |
| Triethyl Citrate, NF | 1.00 |
| Total | 100.0 |

II. Processing Procedures for Manufacturing IPX203 Capsules for IPX203 B14-01 Biostudy Preparation of Component I Povidone was dissolved in the purified water completely, and then the spray pump with povidone solution was calibrated to the target granulation spray rate (40 mL/min). CD, LD, Croscarmellose Sodium were charged into a high shear granulator and dry mixed for 1-5 minutes at impeller speed of 150 rpm and chopper speed of 1800 rpm. While continue mixing, the solution from Step 1 was sprayed into the granulation bowl until all the solution is sprayed, and granulation was continued with purified water if necessary. The granules were collected, and the wet granules were dried in a fluid bed drier (Glatt GPCP-1) at an Inlet temperature of 65° C. until Loss on Drying is not more than 2.5%. The dried granules were passed through Fitzmill, and the material that passes through 30 mesh screen was collected. The collected material was blended with magnesium stearate.

Alternative Preparation of Carbidopa-Containing Granules or Beads

In order to avoid potential carbidopa degradation during wet granulation process, a dry granulation process by roller compaction was developed. In this formulation, shown in Table 14, the procedures are described as below.

Appropriate amount of carbidopa, levodopa, microcrystalline cellulose, and croscarmellose sodium were charged into a suitable mixer. The materials were dry mixed for an appropriate time and then charged into roller compactor at the controlled speed to start the roller compaction process. After roller compaction, the collected compacted sheets of materials were blended with colloidal silicon dioxide for appropriate time, and then milled into dried granules using a suitable mill. Finally the milled granules were blended with magnesium stearate in the blender.

TABLE 14

Composition for Levodopa/Carbidopa IR Granules by Dry Granulation Method

| Ingredient | Composition (w/w %) |
|---|---|
| Carbidopa | 37.0 |
| Levodopa | 35.0 |
| Microcrystalline Cellulose | 20.0 |
| Croscarmellose Sodium | 4.0 |
| Colloidal Silicon Dioxide | 3.0 |
| Magnesium Stearate | 1.0 |
| Total | 100.0 |

The amount and ratio of carbidopa and levodopa may be adjusted as desired, so long as performance of the dried granules or beads are not compromised.

Similarly, controlled release beads containing carbidopa may be prepared by a dry granulation method as provided through the incorporation of rate-controlling excipient, muco-adhesive polymer, and/or enteric coat. Entacapone-containing beads or granules may also be prepared by a dry granulation method.

Preparation of Component II

Preparation of Core Beads for Component II

Povidone was dissolved in the purified water completely, and then calibrate the spray pump with povidone solution to the target granulation spray rate (18 mL/min). LD, Microcrystalline Cellulose, Mannitol and Sodium Lauryl Sulfate were charged into a high shear granulator and dry mixed for 1-5 minutes at impeller speed of 250 rpm and chopper speed of 1800 rpm. The solution from Step 1 was sprayed into the granulation bowl until all the solution is sprayed, and granulation with purified water was continued as necessary. The wet granules were extruded using the extruder (MG 55 Multi Granulator) equipped with a 0.9 mm hole size screen at extruder speed of 75 rpm. The extrudates were collected, and the extrudates so collected were charged into a spheronizer equipped with a 3 mm cross hatch disc. The extrudates were spheronized at speed of 800 rpm for 1-2 mins. The wet beads were dried in a fluid bed drier (Glatt GPCP-1) at an Inlet temperature of 65±10° C. until Loss on Drying is not more than 2.5%. The dried beads were passed through a mechanical sieve (Vibroscreen) equipped with a 24-MG mesh screen at the bottom, and 16-MG mesh screen at the top. The beads that remained on the 24-MG mesh screens were collected into double polyethylene-lined bags, and the oversized and undersized beads were discarded CA/Copovidone Layer Coating (for Prototype II and III for Component II)

Cellulose acetate and copovidone (Kollidon VA64) were dissolved into the mixture of acetone and isopropyl alcohol (IPA) solution (acetone/IPA at weight ratio of 4/1) completely. The pump was calibrated and set at the target spray rate of 15 g/min for the coating. The core beads from above were coated using Glatt GPCG 2 equipped with a Wurster insert at Inlet air temperature of 35° C., Atomization air pressure of 2.0 bars and Wurster partition height of 30 mm. During coating, the inlet air temperature and spray rate were adjusted to maintain the exhaust air temperature between 25±5° C. After the target amount of coating solution was sprayed, the coated beads were dried at an inlet air temperature of 35° C. for 30 minutes. The dried beads were passed through a mechanical sieve (Vibroscreen) equipped with a pan at the bottom and a 14-MG mesh screen at the top. The beads that passed through 14-MG mesh screen were collected and the oversized beads were rejected.

Eudragit® E100 Layer Coating

Acetone, IPA and purified water (at weight ratio acetone/IPA/water of 68/20/12) were dispensed into a stainless steel container and begin stirring using stir bar. While stirring, Triethyl citrate, Amino Methacrylate Copolymer (Eudragit®

E100) were slowly added into the vortex of the mixed solvent. The mixing was continued until the copolymer completely dissolved. While stirring, Talc was slowly dispersed into the vortex of the solution. Mixing was continued until the material completely dispersed. The suspension was stirred throughout the coating process. The spray pump was calibrated to the target coating spray rate (10 g/min) using the solution above. The beads (from Prototype I, and Prototype II and III) were coated using Glatt GPCG 2 equipped with a Wurster insert at Inlet air temperature of 33° C., Atomization air pressure of 2.0 bars and Wurster partition height of 30 mm. During coating, the inlet air temperature and spray rate were adjusted to maintain the exhaust air temperature between 26±5° C. After the target amount of coating solution was sprayed, the coated beads were dried at an inlet air temperature of 35° C. for 30 minutes. The dried beads were passed through a mechanical sieve (Vibroscreen) equipped with a pan at the bottom and a 14-MG mesh screen at the top. The beads that passed through 14-MG mesh screen were collected, and the oversized beads were rejected.

Enteric (Eudragit® L100) Coating

Acetone and Isopropyl Alcohol were dispensed at weight ratio of 40/60 into a stainless steel container and stirred using a stir bar. While stirring, the enteric copolymer Eudragit® L100 and Triethyl Citrate (TEC) were slowly added into the vortex of the mixed solvent. Mixing was continued until the enteric copolymer completely dissolved. While stirring, Talc was slowly dispersed into the vortex of the solution. Mixing continued until the material was completely dispersed. The suspension was continually stirred throughout the coating process. The spray pump was calibrated to the target at a coating spray rate (9 g/min) using the solution above. The Eudragit® E-coated beads were coated using Glatt GPCG 2 equipped with a Wurster insert at Inlet air temperature of 35° C., Atomization air pressure of 2.0 bars and Wurster partition height of 30 mm. During coating, the inlet air temperature, and spray rate was adjusted to maintain the exhaust air temperature between 27±5° C. After the target amount of coating solution was sprayed, the coated beads were dried at an inlet air temperature of 38° C. for 30 minutes. The dried beads were passed through a mechanical sieve (Vibroscreen) equipped with a pan at the bottom and a 14-MG mesh screen at the top. The beads that passed through 14-MG mesh screen were collected, and the oversized beads were rejected.

Preparation of Entacapone Component (for IPX203-C0026)

Povidone was completely dissolved in the purified water. Entacapone, Sodium Starch Glycolate, Sodium Lauryl Sulfate and Microcrystalline Cellulose were charged into a high shear granulator and dry mix for 1-5 minutes at impeller speed of 200-300 rpm and chopper speed of 1400-1600 rpm. The solution was sprayed into the granulation bowl at the spray rate of 19 ml/min until all the solution is used, and granulation continued with Purified Water as necessary. The wet granules were extruded using the extruder (MG 55 Multi Granulator) equipped with a 0.9 mm hole size screen at extruder speed of 55 rpm. The extrudates were collected, and charged into a spheronizer equipped with a 3 mm cross hatch disc. The extrudate were spheronized at a spheronization speed of 650 rpm for 2 mins. The wet beads were dried in a fluid bed drier (Glatt GPCP-1) at an Inlet temperature of 40±5° C. until Loss on Drying is not more than 5.0%. The dried beads were passed through a mechanical sieve (Vibroscreen) equipped with a pan at the bottom, 24-MG mesh screen in the middle, and 16-MG mesh screen at the top. The beads that were retained on 24-MG mesh were collected and the beads on the pan and 16-MG mesh screen were rejected. Acetone and Isopropyl Alcohol were dispensed at weight ratio of 40/60 into a stainless steel container and stirred using a stir bar. While stirring, the enteric copolymer Eudragit® L100 and TEC were slowly added into the vortex of the mixed solvent. Mixing continued until the enteric copolymer completely dissolved. While stirring, Talc was slowly dispersed into the vortex of the solution. Mixing continued until the material was completely dispersed. The suspension was stirred throughout the coating process. The spray pump was calibrated to the target coating spray rate (8 g/min) using the solution. The core beads were coated using Glatt GPCG 1 equipped with a Wurster insert at Inlet air temperature of 35±10° C., Atomization air pressure of 1.5 bars and Wurster partition height of 15-30 mm. During coating, the inlet air temperature, exhaust flap, and spray rate were adjusted to maintain the exhaust air temperature between 27±5° C. After the target amount of coating solution was sprayed, the coated beads were dried at an inlet air temperature of 40° C. for 20 minutes. The dried beads were passed through a mechanical sieve (Vibroscreen) equipped with a pan at the bottom and a 14-MG mesh screen at the top. The beads that passed through 14-MG mesh screen were collected and the oversized beads were rejected.

Encapsulation

The required amounts of the Component I, and Component II Beads and Talc were dispensed. For formulation IPX203-C0026, also Entacapone component beads were also dispensed. Talc was weighed at the weight ratio of beads/Talc at 99/1, and Component II beads and Talc were blended thoroughly. For IPX203-C0026 product, Talc was also weighed at the weight ratio of ENT beads/Talc at 99/1, and Entacapone beads and Talc were blended thoroughly. The Component I granules and Component II beads (from encapsulation section) were encapsulated into size 00 hard gelatin capsules, using MG Flexalab Encapsulator at the target fill weight for IPX203 products IPX203-C0023, -C0024, and -C0025. The Component I granules, Component II beads (from encapsulation section), and entacapone beads (from encapsulation section) were encapsulated into size 00 hard gelatin capsules, using MG Flexalab Encapsulator at the target fill weight for IPX203 products IPX203-C0026.

III. In Vitro LD Release Profiles of Four Formulations for Pharmacokinetic Study (PX203-B14-01)

The in vitro release profiles of the formulations IPX203-C0023, -C0024, -C0025, and -C0026 were measured using USP I dissolution method at agitation speed of 75 rpm in Simulated Gastric Fluid (pH 1.0, without enzyme) for first 2 hrs and followed by in Simulated Intestinal Fluid (pH 7.0, without enzyme). FIG. 6 shows the release profiles of these four formulations. Formulation IPX203-C0025 and IPX203-C0026 contain the same Component II beads thus having same dissolution profiles. The T90 (time duration for 90% of LD released) is approximately 4 hr, 5 h and 7 hrs for -C0023, -C0025 and -C0026, and -C0024, respectively.

IV. In Vivo Evaluation (Biostudy IPX203-B14-01)

The in vivo performance of the prepared products IPX203-C0023, -C0024, -C0025, and -C0026 has been evaluated in 19 healthy volunteers in a relative bioavailability study IPX203-B14-01. IPX203-B4-01 was a single-center, open-label, randomized, single-dose, five-sequence, five-treatment crossover study. During each treatment period subjects received a single dose of the assigned study treatment. There was a minimum 5-day washout between treatments. Blood samples were obtained predose and following dosing for approximately 12 hours for measurement of plasma concentrations. Thirty healthy male and female subjects, 18 to 45 years of age at the time of dosing with a body mass index of 18.0 to 30.0 kg/m$^2$, inclusive, were enrolled. All treatments were administered with 240 mL of room-temperature water to subjects in a fasted state. Subjects were instructed to swallow the study drugs intact without crushing or chewing. FIG. 7 shows the levodopa plasma profiles for all these regimens, and Table 15 shows the PK parameters relative to Stalevo®.

TABLE 15

PK Parameters for All the Regimens Tested in IPX203 B13-01 Study (n = 19)

| Formulation | % of IPX203 Test Formulation/ Stalevo ® | | % of IPX203 Test Formulation/ Stalevo ® (normalized by LD dose) | |
|---|---|---|---|---|
| | $AUC_{0-\infty}$ | $C_{max}$ | $AUC_{0-\infty}$ | $C_{max}$ |
| IPX203-C0023 | 277.3 | 179.4 | 77.0 | 49.8 |
| IPX203-C0024 | 199.1 | 121.4 | 55.3 | 33.7 |
| IPX203-C0025 | 226.9 | 134.0 | 63.0 | 37.2 |
| IPX203-C0026 | 265.9 | 141.6 | 73.9 | 39.3 |

Table 16 shows the duration of time above 50% $C_{max}$ for IPX203-C0023, -C0024, -C0025 and -C0026 and conventional formulations.

TABLE 16

Duration of Time Above 50% Cmax IPX203-C0023, -C0024, -C0025 and -C0026 and Conventional Formulations

| Formulation | N | Median | Mean | % Coefficient of Variation (SD/Mean) |
|---|---|---|---|---|
| IPX203-C0023 | 19 | 4.00 | 4.14 | 29.88 |
| IPX203-C0024 | 19 | 5.38 | 4.84 | 35.94 |
| IPX203-C0025 | 19 | 5.38 | 5.20 | 29.30 |
| IPX203-C0026 | 19 | 4.88 | 5.23 | 36.32 |

$C_{max}$ values normalized to allow comparison

Comparison of the LD plasma concentration profile of the tested formulations to the reference product Stalevo® indicates that: (1) the IPX203 regimens, based on IPX203-C0023, -C0024, -C0025 and -C0026 formulations, showed more extended effect than Stalevo® (Table 16 and FIG. 7); in addition, the IPX203 formulations showed more extended effect than Sinemet® or Sinemet® CR (Table 16 and FIG. 3; for Sinemet® CR (N=11), T>50% Cmax is 3.41 hrs); (2) the IPX203 formulations, namely IPX203-C0023, -C0024, -C0025 and -C0026 formulations, showed relatively flat plasma profiles for LD compared to Stalevo® (FIG. 7); (3) the time duration between 50% of Cmax to Cmax for IPX203-C0023, -C0024, -C0025 and -C0026 formulations are much longer than Stalevo®, (approximately 4.1-5.2 hrs for test formulations, compared to 2.3 hrs for Stalevo®; and (4) the variation of the time duration between 50% Cmax to Cmax for IPX2003-C0023, -C0024, -C0025 and -C0026 formulations is less than Stalevo®.

What is claimed is:

1. A controlled release oral solid formulation comprising
    (a) a controlled release component comprising a core comprising levodopa and/or an ester of levodopa or salts thereof, wherein the core is coated with a first layer comprising a rate-controlling polymer; the first layer is coated with a muco-adhesive layer comprising a dimethylaminoethyl methacrylate copolymer and the muco-adhesive layer is coated with a layer of an enteric coating polymer; and
    (b) an immediate release component comprising levodopa and/or an ester of levodopa or salts thereof; and
    wherein the controlled release component is formulated as a mini-tablet, bead, or granule and produces an in vivo levodopa plasma profile following oral administration of the controlled release oral solid formulation to a subject under fasting conditions comprising:
        (a) a levodopa plasma concentration corresponding to maximum levodopa plasma concentration ($C_{max}$) occurring within 6 hours after administration of the dosage form;
        (b) a time to reach 50% $C_{max}$ of less than one hour; and
        (c) wherein the in vivo plasma level of levodopa is maintained at 50% $C_{max}$ or above for at least 5.0 hours.

2. The controlled release oral solid formulation of claim 1 wherein the immediate release component (b) is formulated as a mini-tablet, bead, or granule.

3. The controlled release oral solid formulation of claim 1 further comprising a decarboxylase inhibitor.

4. The controlled release oral solid formulation of claim 1, wherein the formulation is encapsulated in a capsule.

5. The controlled release oral solid formulation of claim 1, wherein the muco-adhesive layer comprising a dimethylaminoethyl methacrylate copolymer further comprises a polymer selected from the group consisting of polycarbophil, carbomer, cellulosics, chitosan, diethylaminodextran, diethyl aminoethyldextran, polygalactosamine, polylysine, polyornithine, prolamine, polyimine, hyaluronic acid, sodium alginate, sodium carboxymethylcellulose (sodium CMC), and alginate, or a combination thereof.

6. The controlled release oral solid formulation of claim 1, wherein the rate-controlling polymer comprises cellulose acetate or ethylcellulose.

7. The controlled release oral solid formulation of claim 6, wherein the rate-controlling polymer comprises cellulose acetate and copovidone.

8. The controlled release oral solid formulation of claim 1, wherein the enteric coating polymer comprises one or more methacrylic acid copolymers.

9. The controlled release oral solid formulation of claim 1, wherein the ester of levodopa is selected from the group consisting of ethyl (2S)-2-amino-3-(3,4-dihydroxyphenyl) propanoate (levodopa ethyl ester), levodopa butyl ester, and levodopa methyl ester.

10. The controlled release oral solid formulation of claim 9, wherein the ester of levodopa is a salt selected from the group consisting of an octanoate salt, myristate salt, succinate salt, succinate dihydrate salt, fumarate salt, or fumarate dihydrate salt.

11. The controlled release oral solid formulation of claim 1, wherein the controlled release component (a) has an in vitro dissolution profile with less than 20% release of the levodopa or ester of levodopa at about pH 1.0 within two hours using a USP I dissolution method at a speed of 75 and after two hours of testing in the dissolution fluid of about pH 1.0 changing the dissolution to a fluid with a pH of about 7.0, the controlled release component will exhibit an extended release over at least 4 to 8 hours.

12. The controlled release formulation of claim 11, wherein the controlled release component (a) has an in vitro dissolution profile with less than 10% release of the levodopa or ester of levodopa at about pH 1.0 within two hours.

13. The controlled release formulation of claim 1, wherein the in vivo plasma level of levodopa is maintained at 50% $C_{max}$ or above for at least 5.5 hours.

14. The controlled release formulation of claim 1, wherein the in vivo plasma level of levodopa is maintained at 50% $C_{max}$ or above for at least 6.0 hours.

15. The controlled release formulation of claim 1, wherein the in vivo plasma level of levodopa is maintained at 50% $C_{max}$ or above for at least 6.5 hours.

16. The controlled release formulation of claim 1, wherein the in vivo plasma level of levodopa is maintained at 50% $C_{max}$ or above for at least 7.0 hours.

17. A method of treating Parkinson's disease or primary parkinsonism comprising, administering to the subject an effective amount of the controlled release oral solid formulation of claim 1.

18. The controlled release oral solid formulation of claim 1 wherein the controlled release component is a bead exhibiting a size between 0.8 to 1.2 mm.

19. The controlled release oral solid formulation of claim 1 wherein the controlled release component is a bead that passes through a 12 mesh screen but may be retained on a 18, 24, or 25 mesh screen.

20. The controlled release oral solid formulation of claim 1 wherein the controlled release component is a bead that passes through a 14 mesh screen but may be retained on a 18, 24, or 25 mesh screen.

21. The controlled release oral solid formulation of claim 1 wherein the controlled release component is a bead that passes through a 16 mesh screen but may be retained on a 18, 24, or 25 mesh screen.

22. The controlled release oral solid formulation of claim 1 wherein the levodopa, and/or ester of levodopa, and/or salts thereof are dispersed throughout the core or layered on a sugar sphere.

* * * * *